United States Patent
Chung

(10) Patent No.: US 9,315,457 B2
(45) Date of Patent: Apr. 19, 2016

(54) CRYSTALLINE POLYMORPHIC FORMS OF AN ANTIDIABETIC COMPOUND

(71) Applicant: Merck Sharp & Dohme Corp., Rahway, NJ (US)

(72) Inventor: John Y. L. Chung, Edison, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 14/669,664

(22) Filed: Mar. 26, 2015

(65) Prior Publication Data

US 2016/0075650 A1    Mar. 17, 2016

Related U.S. Application Data

(60) Continuation of application No. 14/186,829, filed on Feb. 21, 2014, now Pat. No. 9,012,488, which is a division of application No. 13/144,031, filed as application No. PCT/US2010/020460 on Jan. 8, 2010, now Pat. No. 8,697,740.

(60) Provisional application No. 61/204,886, filed on Jan. 12, 2009.

(51) Int. Cl.
    *C07D 209/18*    (2006.01)

(52) U.S. Cl.
    CPC ................... *C07D 209/18* (2013.01)

(58) Field of Classification Search
    CPC .................................................. C07D 209/18
    See application file for complete search history.

(56) References Cited

U.S. PATENT DOCUMENTS

| | | | |
|---|---|---|---|
| 6,420,398 B2 | 7/2002 | Mita et al. | |
| 7,687,534 B2 | 3/2010 | Stelmach et al. | |
| 7,968,589 B2 | 6/2011 | Stelmach et al. | |
| 8,697,740 B2 | 4/2014 | Chung et al. | |
| 8,889,683 B2 | 11/2014 | Cheng et al. | |
| 9,012,488 B2 | 4/2015 | Chung et al. | |
| 2007/0276027 A1 | 11/2007 | Campeta et al. | |
| 2008/0085926 A1 | 4/2008 | Stelmach et al. | |

FOREIGN PATENT DOCUMENTS

WO    2010/080971 A1    7/2010

OTHER PUBLICATIONS

International Search Report of PCT/US2010/20460, mailed Mar. 9, 2010.

*Primary Examiner* — Shawquia Jackson

(57) ABSTRACT

The present invention relates to polymorphic forms of a compound of formula A:

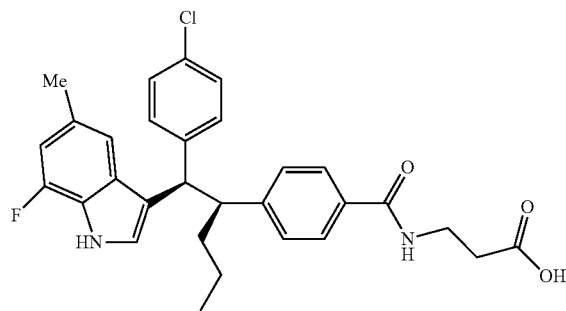

A

This compound is useful as a glucagon receptor antagonist and serves as a pharmaceutically active ingredient for the treatment of type 2 diabetes and related conditions, such as hyperglycemia, obesity, dyslipidemia, and the metabolic syndrome. Hydrates, hemihydrates, anhydrates and similar polymorphic forms are included.

4 Claims, 16 Drawing Sheets

X-ray powder diffraction (XRPD) pattern of free acid hydrate polymorphic Form I of Compound A.

13C solid state NMR of free acid
hydrate polymorphic Form I of Compound A.

X-ray powder diffraction (XRPD) pattern of anhydrous free acid polymorphic Form I of Compound A.

X-ray diffraction pattern of the crystalline anhydrate Form II.

Thermogravimetric analysis curve of the crystalline anhydrate Form II.

Differential scanning calorimetry curve of the crystalline anhydrate Form II.

Solid sate C-13 CPMAS NMR spectrum for the crystalline anhydrate Form II.

Fluorine-19 Single Pulse Excitation
MAS spectrum of Anhydrate II.

X-ray diffraction pattern of the crystalline anhydrate Form III.

Differential scanning calorimetry curve of the crystalline anhydrate Form III.

Fluorine-19 Single Excitation MAS spectrum of crystalline anhydrate Form III.

CRYSTALLINE POLYMORPHIC FORMS OF AN ANTIDIABETIC COMPOUND

CROSS-REFERENCE TO RELATED APPLICATIONS

The present application is a continuation application of U.S. application Ser. No. 14/186,829, filed Feb. 21, 2014, which is a divisional application of U.S. application Ser. No. 13/144,031 (now U.S. Pat. No. 8,697,740), filed Sep. 23, 2011 as a U.S. National Phase application under 35 U.S.C. §371 of PCT/US2010/020460, filed Jan. 8, 2010, which claims priority from U.S. provisional Application Ser. No. 61/204,886, filed Jan. 12, 2009. The present application claims priority to the foregoing applications.

FIELD OF THE INVENTION

The present invention relates to novel polymorphic forms of a compound of formula A. This compound is useful as a pharmaceutically active ingredient for the treatment of type 2 diabetes and related conditions, such as hyperglycemia, obesity, dyslipidemia, and the metabolic syndrome.

BACKGROUND OF THE INVENTION

Type 2 diabetes remains a serious medical problem. There is an ongoing need for new treatments that are more effective and that have fewer side effects. Glucagon receptor antagonists are important upcoming medications for the treatment of type 2 diabetes and the present compound is particularly useful in this regard.

SUMMARY OF THE INVENTION

The present invention relates to polymorphic forms of a compound of formula A:

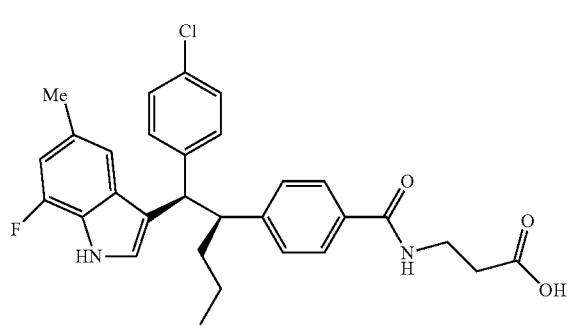

A

The compound is also known as N-(4-{(1S)-1-[(R)-(4-chlorophenyl)(7-fluoro-5-methyl-1H-indol-3-yl)methyl]butyl}benzoyl)-β-alanine. Compound A has been disclosed in a published PCT patent application, WO2008/042223 published on Apr. 10, 2008. Polymorphic forms of the compound that are particularly useful in the preparation of pharmaceutical products are described herein.

The invention also relates to pharmaceutical compositions comprising the polymorphic forms described herein, methods for the preparation thereof and the like

BRIEF DESCRIPTION OF THE DRAWINGS

The invention is described in connection with the drawings appended hereto, in which.

DETAILED DESCRIPTION OF THE INVENTION

Figure 1:
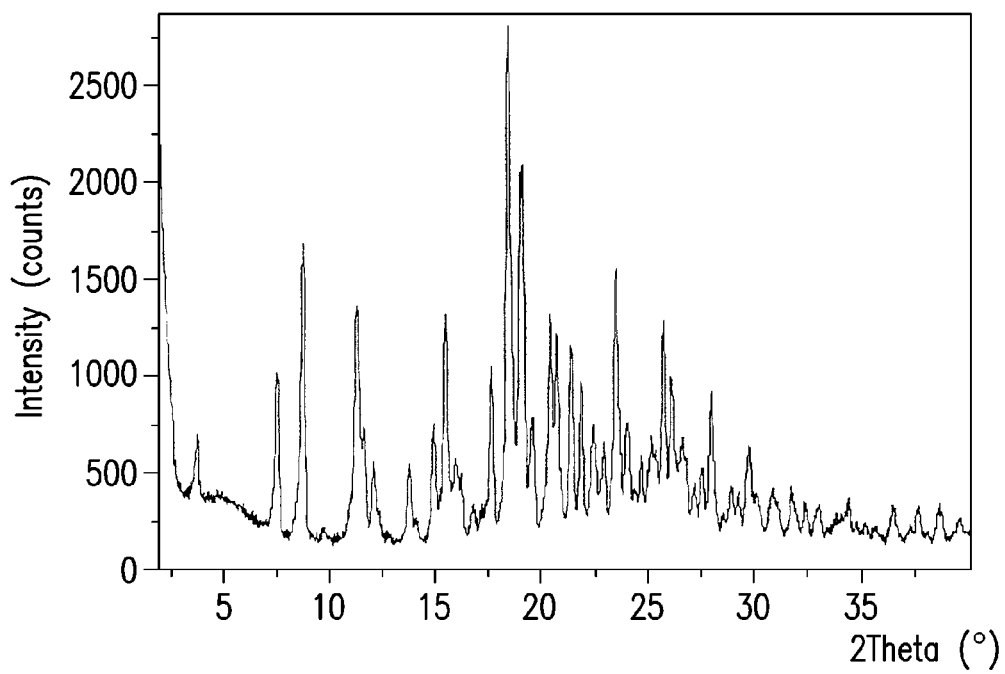
FIG. 1 is the X-ray powder diffraction (XRPD) pattern for the free acid hydrate polymorphic Form I of Compound A.

The present invention provides a process for the preparation of crystalline N-(4-{(1S)-1-[(R)-(4-chlorophenyl)(7-fluoro-5-methyl-1H-indol-3-yl)methyl]butyl}benzoyl)-β-alanine of structural formula A:

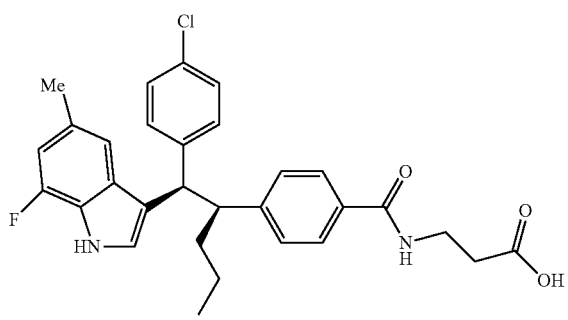

A and specifically polymorphic forms thereof, including solvates.

Crystal forms are convenient for the preparation and isolation of compound A with an upgrade in purity, and represent a convenient scalable way to produce high purity compound A. Crystalline forms were identified including the crystalline free base of Compound A as an alcohol solvate and various crystalline salt forms of Compound A are included as well. These crystalline salts of compound A are novel and have improved physiochemical properties, such as purity, stability and ease of formulation that render them particularly suitable for the manufacture of pharmaceutical dosage forms. Discovery of crystalline forms allowed for the *facile* purification, isolation, and formulation of compound A.

The abbreviations in the table below have the following meanings:

| | |
|---|---|
| Me = methyl | Et = ethyl |
| t-Bu = t-butyl | IPA = isopropyl alcohol |
| Ac = Acetyl | THF = tetrahydrofuran |
| DCM = dichloromethane | DIEA = diisopropylethylamine |
| DMF = dimethylformamide | DPE phos = Bis(2-diphenylphosphinophenyl)ether |
| IPAC = isopropylacetate | MTBE = methyl t-butyl ether |
| BINAP = 2,2'-bis(diphenylphosphino)-1,1'-binaphthyl | Tol-BINAP = 2,2'-bis(di-p-tolylphosphino)-1,1'-binaphthyl |

One aspect of the invention that is of interest relates to process for synthesizing a compound of formula A:

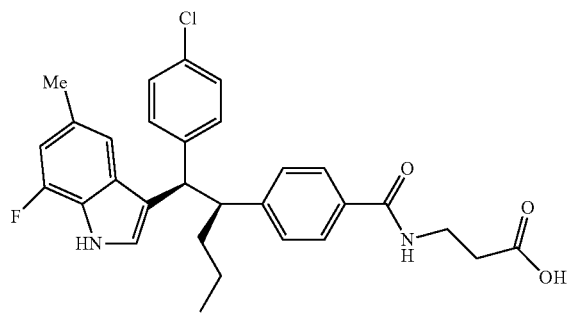

A comprising deprotecting a compound of formula 11a:

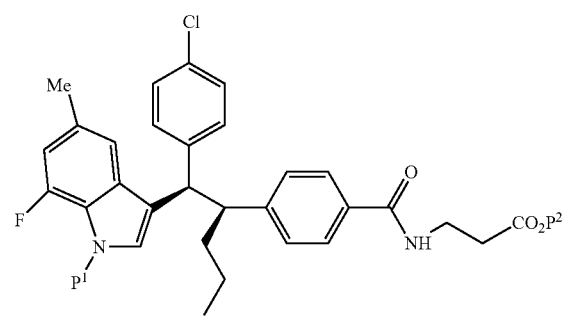

11a wherein P¹ and P² represent protecting groups, to produce a compound of formula A.

Another aspect of the invention relates to a process for synthesizing a compound of formula A:

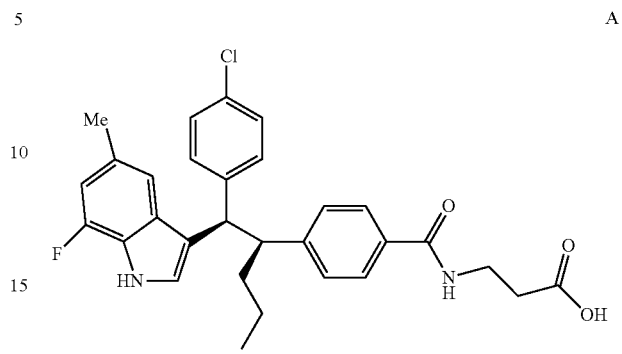

A comprising reacting a compound of formula 10a:

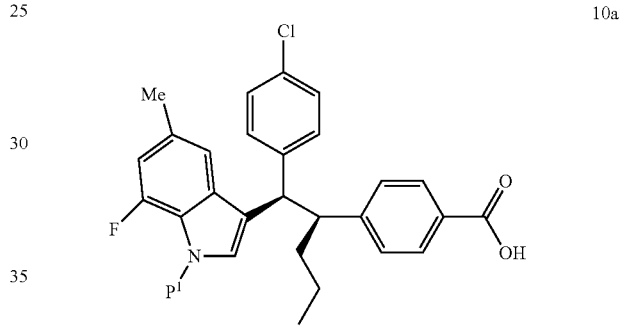

10a wherein P¹ represents a protecting group with a beta alanine ester of the formula

wherein P² represents a protecting group, with a peptide coupling agent, to produce a compound of formula 11a:

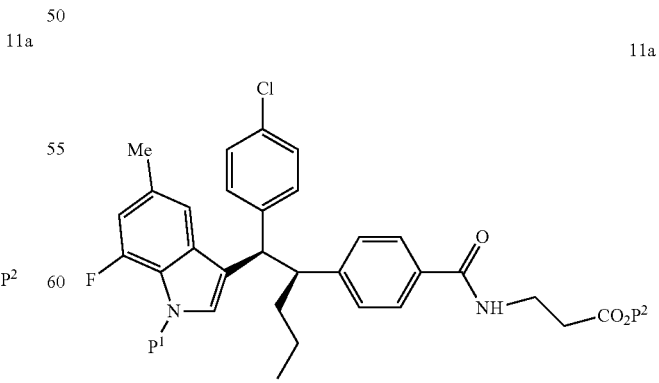

11a and deprotecting compound 11a to produce a compound of formula A.

Another aspect of the invention relates to a A process for the synthesis of a compound of formula A:

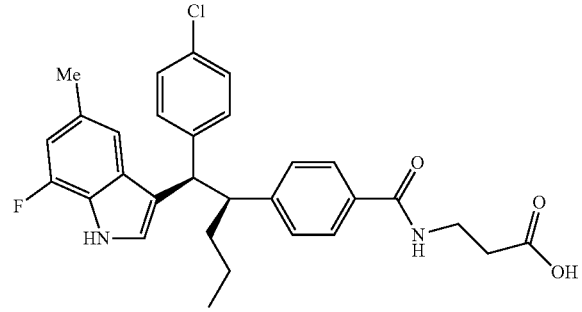

A comprising reacting a compound of the formula 11:

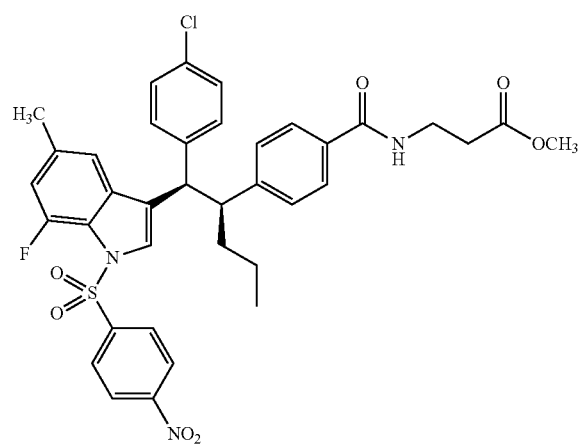

11 with base to produce a compound of formula A.

Another aspect of the invention relates to a process as described above wherein the base is NaOH.

Another aspect of the invention relates to a process for synthesizing a compound of formula A as shown above.

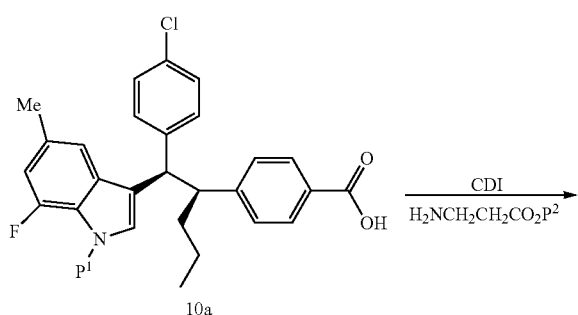

10a $\xrightarrow{\text{CDI}}$
$H_2NCH_2CH_2CO_2P^2$

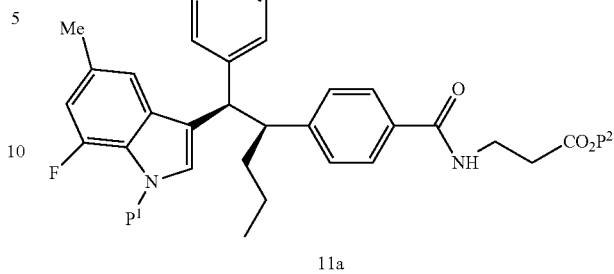

11a

A compound of formula 10a is reacted with N,N-carbonyldiimidazole (CDI) or another peptide coupling reagent and a beta-alanine ester $H_2NCH_2CH_2CO_2P^2$ to produce a compound of formula 11a. $P^1$ represents a protecting group suitable for protection of the indole nitrogen atom. Representative examples include nosyl, benzyl, tolyl and similar groups, with nosyl being preferred. Suitable protecting groups for the beta alanine ester, $P^2$, include small alkyl groups, such as methyl. Thereafter deprotection is undertaken to remove $P^1$ and $P^2$, thus forming a compound of formula A.

A synthetic route for the compound of formula A has been disclosed in WO2008/042223 published on Apr. 10, 2008, hereby incorporated by reference, and is set forth below. In the present invention, seed crystals of compound were generated from lab scale runs and formed before or after chromatographic purification.

Intermediate 1

Racemic 4-[2-(4-chlorophenyl)-1-propylpent-4-en-1-yl]benzoic acid

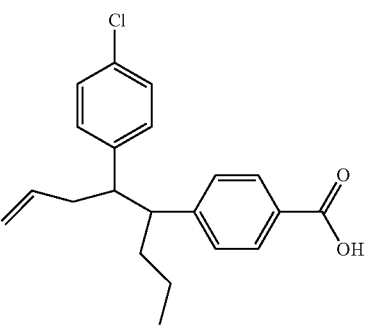 [SMILES: C=CCC(c1ccc(Cl)cc1)C(CCC)c1ccc(C(=O)O)cc1]

Step A. tert-Butyl 4-[2-(4-chlorophenyl)-2-oxoethyl]benzoate

A THF solution (200 ml) containing t-butyl 4-bromobenzoate (19.9 g, 77.6 mmol), 4-chloroacetophenone (10 g, 64.7 mmol), $Pd_2dba_3$ (1.19 g, 1.29 mmol), BINAP (1.6 g, 2.58 mmol) and NaOtBu (8.7 g, 90.6 mmol) was refluxed under an argon atmosphere for approximately 5 hours. The solution was concentrated and then partitioned between EtOAc and water. The organic phase was washed with water, brine and dried over $Na_2SO_4$. The filtered solution was concentrated and the residue purified by silica gel chromatography using a hexanes/EtOAc gradient to give the title compound. $^1$H NMR (500 MHz, CDCl₃): δ 7.95 (d, J=8.5 Hz, 2H); 7.93 (d, J=8.7 Hz, 2H); 7.43 (d, J=8.3 Hz, 2H); 7.29 (d, J=8.2 Hz, 2H); 4.30 (s, 2H); 1.58 (s, 9H). LC1 4.01 min. (M-tBu+H)=275

Step B. tert-Butyl 4-[1-(4-chlorobenzoyl)butyl]benzoate

KOtBu (2.55 g, 22.7 mmol) was added to a cooled (ice bath) THF solution (40 ml) containing the intermediate from Step A (5.0 g, 15.15 mmol). After 10 minutes n-propyl iodide (3 ml, 30.3 mmol) was added dropwise. The ice bath was removed and the reaction was monitored by MS-HPLC analysis. The solution was then partitioned (<1 hour) between EtOAc and water. The organic phase was washed with water, brine and dried over Na₂SO₄. The filtered solution was concentrated and the residue purified by silica gel chromatography using a hexanes/EtOAc gradient to give the title compound. ¹H NMR (400 MHz, CDCl₃): δ 7.90 (d, J=7.8 Hz, 2H); 7.84 (d, J=8.6 Hz, 2H); 7.33 (d, J=8.6 Hz, 2H); 7.31 (d, J=8.3 Hz, 2H); 4.51 (t, J=7.2 Hz, 1H); 2.18-2.08 (m, 1H); 1.84-1.68 (m, 1H); 1.54 (s, 9H); 1.38-1.18 (m, 2H); 0.90 (t, J=7.3 Hz, 3H). LC1 4.43 min. (M-tBu+H)=317

Step C. tert-Butyl 4-{1-[(4-chlorophenyl)(hydroxy)methyl]butyl}benzoate

NaBH₄ (0.5 g, 13.21 mmol) was added in portions to a MeOH solution (40 ml) containing the intermediate from Step B (3.78 g, 10.16 mmol). After stirring for 1 hour the solution was concentrated and the residue partitioned between EtOAc and water. The organic phase was washed with water, brine and dried over Na₂SO₄. The filtered solution was concentrated and the residue purified by silica gel chromatography using a hexanes/EtOAc gradient to give the title compound as a >10:1 ratio of diastereomers. ¹H NMR (400 MHz, CDCl₃): δ 7.93 (d, J=8.3 Hz, 2H); 7.28 (d, J=8.4 Hz, 2H); 7.23 (d, J=8.4 Hz, 2H); 7.18 (d, J=8.4 Hz, 2H); 4.73 (d, J=7.8 Hz, 1H); 2.89-2.83 (m, 1H); 1.58 (s, 9H); 1.57-1.56 (m, 1H); 1.41-1.33 (m, 1H); 1.09-0.91 (m, 2H); 0.72 (t, J=7.3 Hz, 3H). LC1 4.22 min. (M-tBu-OH+H)=301

Step D. 4-[2-(4-Chlorophenyl)-1-propylpent-4-en-1-yl]benzoic acid

A 1,2-dichloroethane (DCE) (20 ml) solution containing the intermediate from Step C (1.81 g, 4.84 mmol), allyl trimethylsilane (6.2 ml, 38.7 mmol) and boron trifluoride etherate (1.84 ml, 14.5 mmol) was heated at 80° C. for 1.5 hours. The solution was cooled to room temperature and methanol (10 ml) was slowly added. The solution was then concentrated and the residue partitioned between EtOAc and aqueous 1N HCl. The organic phase was washed with water, brine and dried over Na₂SO₄. The filtered solution was concentrated to give the title compound (as a ca 3:1 mixture of diastereomers) which was used without further purification. A portion was purified for spectral analysis. Data is for the major diastereomer ¹H NMR (400 MHz, CDCl₃): δ 8.07 (d, J=8.3 Hz, 2H); 7.30 (d, J=5.7 Hz, 2H); 7.28 (d, J=5.4 Hz, 2H); 7.08 (d, J=8.3 Hz, 2H); 5.42-5.32 (m, 1H); 4.79-4.66 (m, 2H); 2.83-2.77 (m, 2H); 2.11-2.05 (m, 2H); 1.43-1.29 (m, 2H); 1.00-0.80 (m, 2H); 0.68 (t, J=7.3 Hz, 3H). LC1 4.08 min. (M+H)=343

NMR experiments (NOE) on advanced compounds (see EXAMPLE 1) derived from INTERMEDIATE 1 established the relative stereochemistry of the minor and major diastereomers of INTERMEDIATE 1 as:

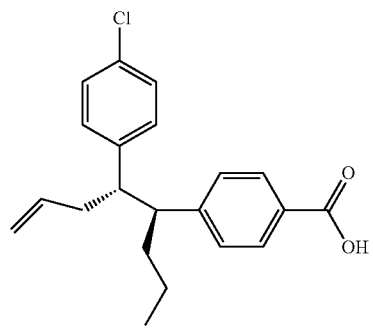

Minor Diastereomer

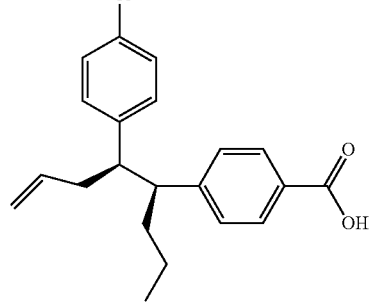

Major Diastereomer

Intermediate 2

4-[(1S,2R)-2-(4-chlorophenyl)-1-propylpent-4-en-1-yl]benzoic acid

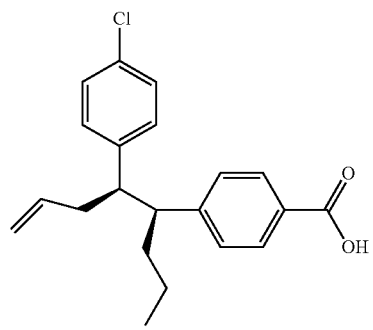 [SMILES: C=CC[C@@H](c1ccc(Cl)cc1)[C@H](CCC)c1ccc(C(=O)O)cc1]

Step A. 2-(4-Bromophenyl)-N-[(1R,2R)-2-hydroxy-1-methyl-2-phenylethyl]-N-methylacetamide Pivaloyl chloride (7.8 ml, 63.3 mmol) was added dropwise to a DCM/THF solution (100 ml/20 ml) containing 4-bromophenylacetic acid (13.59 g, 63.2 mmol). DIEA (11.0 ml, 63.1 mmol) was then added dropwise (exotherm). After stirring at room temperature for 1 hour the solution was poured slowly into a DCM/THF solution (100 ml/20 ml) containing (1R,2R)-(−)-pseudoephedrine (10.5 g, 63.5 mmol) and DIEA (11.0 ml, 63.1 mmol). After stirring overnight at room temperature the solution was concentrated and the residue partitioned between EtOAc and water. The organic phase was washed with aqueous 1N NaOH (2×), aqueous 1N HCl (3×), brine and dried over MgSO₄. The solution was filtered and concentrated. The oil residue was diluted with 100 ml of toluene and concentrated. The residue was then dissolved in ethyl ether and triturated with hexanes to give the title compound as a white solid. The compound is a 3:1 mixture of amide rotational isomers by proton NMR: $^1$H NMR (400 MHz, asterisk denotes minor rotamer, CDCl$_3$): δ 7.42 (d, J=8.3 Hz, 2H); 7.39-7.27 (m, 5H); 7.11*(d, J=8.4 Hz, 2H); 7.04 (d, J=8.3 Hz, 2H); 4.64-4.42 (m, 1H); 4.07-3.94 (m, 1H); 3.82-3.70 (m, 1H); 2.94*(s, 3H); 3.63 (s, 2H); 2.82 (s, 3H); 1.12 (d, J=7.0 Hz, 3H); 0.86*(d, 3H, J=7.0 Hz). LC1 3.23 min. (M+H)=362

Step B. 2-(4-Bromophenyl)-N-[(1R,2R)-2-hydroxy-1-methyl-2-phenylethyl]-N-methylpentanamide THF (40 ml) was added to dry lithium chloride (8 g, 189 mmol) and diisopropyl amine (9.2 ml, 65.6 mmol) under an argon atmosphere. The suspension was cooled to −78° C. and n-BuLi (1.6M in hexanes, 37.9 ml, 60.6 mmol) was added dropwise. After stirring for 5 minutes the solution was warmed to 0° C. After 5 minutes the solution was cooled to −78° C. and a THF solution (45 ml) containing the intermediate from Step A (10.56 g, 29.15 mmol) was added dropwise. The solution was then stirred at −78° C. for 1 hour and then warmed to 0° C. After 15 minutes n-propyl iodide (4.3 ml, 44.1 mmol) was added dropwise. The solution was stirred at 0° C. for approximately 2 hours. To the reaction mixture was added saturated aqueous NH$_4$Cl and EtOAc. The phases were separated and the aqueous phase extracted with EtOAc. The combined organic phases were dried over Na$_2$SO$_4$, filtered and concentrated. The oil residue was dissolved in ethyl ether/hexanes (4/6) and filtered through a short plug of silica gel. The filtered solution was concentrated to give the title compound. The compound is a 3:1 mixture of amide rotational isomers by proton NMR: $^1$H NMR (400 MHz, asterisk denotes minor rotamer, CDCl$_3$): δ 7.42 (d, J=8.4 Hz, 2H); 7.41-7.27 (m, 5H); 7.08 (d, J=8.4 Hz, 2H); 4.56 (q, J=6.7 Hz, 1H); 4.42 (br s 1H); 4.17-4.01*(m, 1H); 3.85*(t, J=7.1 Hz, 1H); 3.55 (t, J=7.2 Hz, 1H); 3.00* (s, 3H); 2.72 (s, 3H); 2.07-1.92 (m, 1H); 1.69-1.58 (m, 1H); 1.33-1.13 (m, 2H); 1.11 (d, J=7.0 Hz, 3H); 0.88 (t, J7.3 Hz, 3H): 0.58* (d, J=6.9 Hz, 3H). LC1 3.76 min. (M+H)=404

Step C. 2-(4-Bromophenyl)-1-(4-chlorophenyl)pentan-1-one n-Butyl lithium (1.0M in THF, 59 ml, 94.5 mmol) was added dropwise to a −78° C. THF solution (200 ml) containing 4-chloro bromobenzene (22.63 g, 118.2 mmol) under an argon atmosphere. After 10 minutes a THF solution (30 ml) of the intermediate from Step B (15.88 g, 39.4 mmol) was added dropwise. The solution was warmed to 0° C. and stirred for 30 minutes. Diisopropylamine (5.6 ml, 39.4 mmol) was then added dropwise. After 10 minutes the reaction solution was diluted with 200 ml of AcOH/ethyl ether (1/10 by volume). The mixture was partitioned between EtOAc and saturated aqueous NaHCO$_3$ (foaming). The organic phase was washed with saturated aqueous NaHCO$_3$, water, brine and dried over Na$_2$SO$_4$. The filtered solution was concentrated and the residue purified by silica gel chromatography using hexanes/EtOAc gradient to give the title compound. $^1$H NMR (500 MHz, CDCl$_3$): δ 7.86 (d, 2H, J=8.5 Hz); 7.41 (d, 2H, J=8.5 Hz); 7.37 (d, 2H, J=8.5 Hz); 7.15 (d, 2H, J=8.5 Hz); 4.45 (t, J=7.3 Hz, 1H); 2.15-2.07 (m, 1H); 1.81-1.73 (m, 1H); 1.33-1.19 (m, 2H); 0.91 (t, J=7.4 Hz, 3H). LC1 4.25 min. Not ionized

Step D. 2-(4-Bromophenyl)-1-(4-chlorophenyl)pentan-1-ol

Sodium borohydride (917 mg, 24.25 mmol) was added to a MeOH solution (25 ml) containing the intermediate from Step C (6.53 g, 18.66 mol). After stirring for 1 hour at room temperature the solution was concentrated and the residue partitioned between water and EtOAc. The organic phase was washed with water, brine and dried over Na$_2$SO$_4$. The filtered solution was concentrated to give the title compound as an 8:1 mixture of diastereomers which was used in the next step without further purification. $^1$H NMR for major diastereomer (500 MHz, CDCl$_3$): δ 7.44 (d, J=8.1 Hz, 2H); 7.30 (d, J=8.5 Hz, 2H); 7.19 (d, J=8.5 Hz, 2H); 7.07 (d, J=8.1 Hz, 2H); 4.71-4.68 (m, 1H); 2.81-2.74 (m, 1H); 1.56-1.48 (m, 1H); 1.42-1.32 (m, 1H); 1.12-0.95 (m, 2H); 0.75 (t, J=7.3 Hz, 3H). LC1 4.00 min. (M-OH)=335

Step E. 1-Bromo-4-[2-(4-chlorophenyl)-1-propyl-pent-4-en-1-yl]benzene

The title compound was prepared from the intermediate from Step D using the conditions described in Step D. The title compound is obtained as a 2.1:1 mixture of diastereomers. $^1$H NMR for major diastereomer (500 MHz, CDCl$_3$): δ 7.44 (d, J=8.5 Hz, 2H); 7.28 (d, J=8.3 Hz, 2H); 7.05 (d, J=8.2 Hz, 2H); 7.02 (d, J=8.4 Hz, 2H); 5.46-5.35 (m, 1H); 4.82-4.71 (m, 2H); 2.77-2.62 (m, 2H); 2.14-2.02 (m, 2H); 1.35-1.25 (m, 2H); 1.05-0.89 (m, 2H); 0.67 (t, J=7.3 Hz, 3H). LC1 4.66 min. Not ionized

Step F. n-Butyl 4-[2-(4-chlorophenyl)-1-propylpent-4-en-1-yl]benzoate

An n-butanol solution (5 ml) containing the intermediate from Step E (108 mg, 0.286 mmol), DIEA (0.15 ml, 0.86 mmol) and PdCl$_2$(PPh$_3$)$_2$ (376 mg, 0.06 mmol) was heated at 115° C. under a carbon monoxide atmosphere (balloon). After 1 hour the solution was cooled and concentrated. The residue was dissolved in EtOAc and filtered. The residue was used without purification in the next step. A portion was purified for spectral analysis. $^1$H NMR for major diastereomer (500 MHz, CDCl$_3$): δ 8.00 (d, J=8.3 Hz, 2H); 7.28 (d, J=8.4 Hz, 2H); 7.23 (d, J 8.3 Hz, 2H): 7.07 (d J=8.4 Hz, 2H); 5.42-5.31 (m, 1H); 4.77-4.66 (m, 2H); 4.33 (t, J=6.6 Hz, 2H); 2.80-2.75 (m, 2H); 2.10-2.06 (m, 2H); 1.81-1.68 (m, 2H); 1.41-1.24 (m, 4H); 0.99 (t, J=7.4 Hz, 3H); 0.98-0.86 (m, 4H); 0.67 (t, J=7.3 Hz, 3H). LC1 4.73 min. (M+H)=399

Step G. 4-[(1S,2R)-2-(4-chlorophenyl)-1-propylpent-4-en-1-yl]benzoic acid

A THF/MeOH/water (8 ml/8 ml/3 ml) solution containing the intermediate from Step F (790 mg, 1.98 mmol) and lithium hydroxide monohydrate (406 mg, 9.90 mmol) was stirred overnight at room temperature. The solution was concentrated and the nonvolatile portion was partitioned between aqueous 2N hydrochloric acid and EtOAc. The organic phase was dried over Na$_2$SO$_4$, filtered and concentrated to give the title compound. $^1$H NMR (500 MHz, DMSO-d$_6$): δ 7.90 (d, J=8.2 Hz, 2H); 7.39 (d, J=8.5 Hz, 2H); 7.36 (d, J=8.5 Hz, 2H); 7.26 (d, J=8.4 Hz, 2H); 5.36-5.26 (m, 1H); 4.71-4.60 (m, 2H); 2.94-2.84 (m, 2H); 2.13-2.07 (m, 1H); 1.95-1.87 (m, 1H); 1.42-1.34 (m, 1H); 1.19-1.11 (m, 1H); 0.85-0.77 (m, 2H); 0.60 (t, J=7.3 Hz, 3H). LC3 2.57 min (M+H) 343

Alternatively, the title compound can be prepared from the intermediate from Step E. A pentane solution of t-BuLi (1.7M, 3.08 ml, 5.23 mmol) was added dropwise to a THF solution (20.1 ml) of the intermediate from Step E (760 mg, 2.01 mmol) cooled to −78° C. After 5 minutes, $CO_2$ gas was bubbled for a half minute through the solution. The cooling bath was removed and the solution was warmed to room temperature. The solution was then diluted with aqueous 2N HCl and extracted with EtOAc (2×). The combined organic phases were dried over $Na_2SO_4$, filtered and concentrated to give the title compound.

The absolute stereochemistry of the minor and major diastereomers of INTERMEDIATE 2 is shown below. This assignment is based on the known configuration of the n-propyl substituted carbon, which is derived from the (−)-pseudoephedrine, and NMR experiments (NOE). See WO2008/042223.

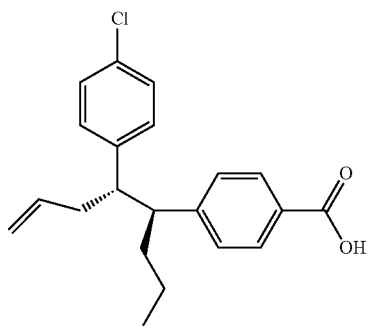

Minor Diastereomer

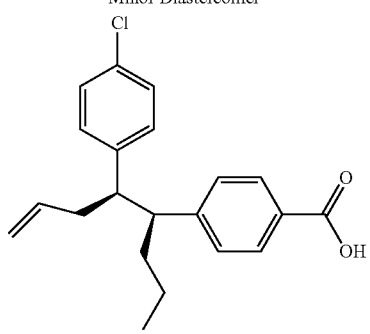

Major Diastereomer

Intermediate 3

Methyl N-{4-[2-(4-chlorophenyl)-1-propylpent-4-en-1-yl]benzoyl}-β-alaninate

A DMF solution (20 ml) containing INTERMEDIATE 1 (1.66 g, 4.84 mmol), methyl β-alaninate hydrochloride (1.01 g, 7.26 mmol), DIEA (4.3 ml, 24.2 mmol) and BOP (3.21 g, 7.26 mmol) was stirred at room temperature for 1.5 hours. The solution was diluted with EtOAc and washed with water, brine and dried over $Na_2SO_4$. The filtered solution was concentrated and the residue purified by silica gel chromatography using a hexanes/EtOAc gradient to give the title compound. $^1$H NMR for the major diastereomer (500 MHz, $CDCl_3$): δ 7.72 (d, J=8.2 Hz, 2H); 7.28 (d, J=8.3 Hz, 2H); 7.22 (d, J=8.2 Hz); 7.07 (d, J=8.4 Hz, 2H); 6.85-6.81 (m, 1H); 5.41-5.31 (m, 1H); 4.77-4.66 (m, 2H); 3.75-3.70 (m, 2H); 3.73 (s, 3H); 2.81-2.72 (m, 2H); 2.67 (t, J=5.9 Hz, 2H); 2.10-2.05 (m, 2H); 1.40-1.29 (m, 2H); 0.98-0.85 (m, 2H); 0.66 (t, J=7.3 Hz, 3H). LC1 4.03 min. (M+H)=428

Intermediate 4

Methyl N-{4-[2-(4-chlorophenyl)-4-oxo-1-propylbutyl]benzoyl}-β-alaninate

Ozone was purged through a chilled (−78° C.) DCM solution (20 ml) containing INTERMEDIATE 3 (1.59 g, 3.72 mmol). The ozone purge was maintained until an excess of ozone was observed (blue color, <10 minutes). The solution was then purged with nitrogen to dissipate the excess ozone. To the solution was added dimethylsulfide (1 ml) followed by triphenylphosphine (977 mg, 3.72 mmol). The solution was warmed to room temperature and stirred for approximately 2 hours. The solution was concentrated and the residue purified by silica gel chromatography using a hexanes/EtOAc gradient to give the title compound. $^1$H NMR for the major diastereomer (500 MHz, $CDCl_3$): δ 9.34 (s, 1H); 7.73 (d, J=8.2 Hz, 2H); 7.30 (d, J=8.3 Hz, 2H); 7.23 (d, J=8.0 Hz, 2H); 7.16 (d, J=8.4 Hz, 2H); 6.87-6.83 (broad s, 1H); 3.72 (s, 3H); 3.75-3.71 (m, 2H); 3.36-3.31 (m, 1H); 2.80-2.72 (m, 1H); 2.69-2.63 (m, 2H); 2.61-2.52 (m, 1H); 2.38 (dd, J=3.9, 17.1 Hz, 1H); 1.45-1.28 (m, 2H); 1.06-0.78 (m, 2H); 0.66 (t, J=7.3 Hz, 3H). LC1 3.55 min. (M+H)=430

Example 1

N-(4-{(1S)-1-[(R)-(4-chlorophenyl)(7-fluoro-5-methyl-1H-indol-3-yl)methyl]butyl}benzoyl)-β-alanine

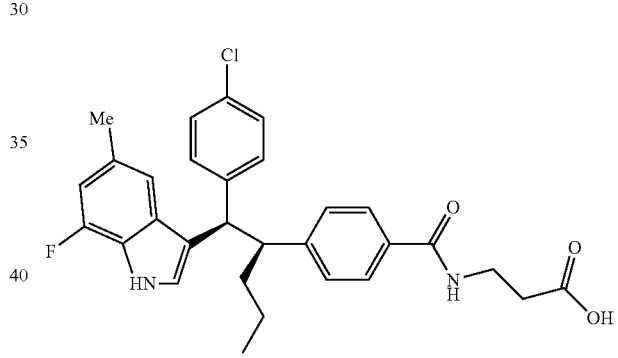

Step A. Methyl N-(4-{(1S)-1-[(R)-(4-chlorophenyl)(7-fluoro-5-methyl-1H-indol-3-yl)methyl]butyl}benzoyl)-β-alaninate (Compound A)

An acetic acid solution (10 ml) of methyl N-{4-[2-(4-chlorophenyl)-4-oxo-1-propylbutyl]benzoyl}-β-alaninate, INTERMEDIATE 4, (757 mg, 1.76 mmol), $ZnCl_2$ (3.1M in AcOH, 1.7 ml, 5.27 mol) and 2-fluoro-4-methylphenylhydrazine hydrochloride (374 mg, 2.1 mmol) was heated at 80° C. for 45 minutes. The solution was concentrated and the residue partitioned between EtOAc and water. The organic phase was washed with water (2×), brine (2×) and dried over $Na_2SO_4$. The solution was filtered, concentrated and the residue purified by silica gel chromatography using a hexanes/ethyl acetate gradient to give the title compound. Data for the major diastereomer: $^1$H NMR (500 MHz, CD3CN): δ 9.11 (s, 1H); 7.54 (d, J=8.2 Hz, 2H); 7.48 (d, J=8.5 Hz, 2H); 7.38 (d, J=8.2 Hz, 2H); 7.30 (d, J=8.4 Hz, 2H); 7.15 (d, J=2.5 Hz, 1H); 7.11 (s, 1H); 7.02-6.97 (m, 1H); 6.59 (d, J=12.3 Hz, 1H); 4.49 (d, J=11.6 Hz, 1H); 3.60 (s, 3H); 3.56-3.48 (m, 3H); 2.52 (t, J=6.8 Hz, 2H); 2.32 (s, 3H); 1.49-1.35 (m, 2H); 1.04-0.90 (m, 2H); 0.69 (t, J=7.4 Hz, 3H). LC1=3.94 min. (M+H)=535. Chiral LC1 (1% to 15% EtOH/heptane over 25 min, 15% EtOH/heptane isocratic >25 min) retention time=28.38 minutes. The material also contains ca 2% by area of the enantiomer. Chiral LC1 (1% to 15% EtOH/heptane over 25 min, 15% EtOH/heptane isocratic >25 min) retention time=26.88 minutes.

Step B. N-(4-{(1S)-1-[(R)-(4-Chlorophenyl)(7-fluoro-5-methyl-1H-indol-3-yl)methyl]butyl}benzoyl)-β-alanine The isomers obtained in Step A were hydrolyzed using the conditions described in INTERMEDIATE 2, Step G. The crude hydrolysis was purified by HPLC to give the title compounds.

Data for the Minor Diastereomer:
$^1$H NMR (400 MHz, CD$_3$CN): δ 9.39 (s, 1H); 7.56 (d, J=8.0 Hz, 2H); 7.37 (d, J=2.4 Hz, 1H); 7.33 (s, 1H); 7.29 (d, J=8.0 Hz, 2H); 7.20 (d, J=8.4 Hz); 7.07 (broad s, 1H); 7.01 (d, J=8.4 Hz, 2H); 6.72 (d, J=12.4 Hz, 1H); 4.45 (d, J=11.6 Hz); 3.65-3.55 (m, 1H); 3.52 (q, J=6.4 Hz, 2H); 2.55 (t, J=6.8 Hz, 2H); 2.40 (s, 3H); 1.84-1.73 (m, 1H); 1.63-1.52 (m, 1H); 1.10-0.93 (m, 2H); 0.71 (t, J=7.2 Hz, 3H). LC1=3.66 min. (M+H)=521.

Data for the major diastereomer: $^1$H NMR (500 MHz, CD$_3$CN): δ 9.11 (s, 1H); 7.56 (d, J=8.2 Hz, 2H); 7.49 (d, J=8.4 Hz, 2H); 7.39 (d, J=8.2 Hz, 2H); 7.31 (d, J=8.4 Hz, 2H); 7.16 (d, J=2.4 Hz, 1H); 7.12 (s, 1H); 7.04 (s, 1H); 6.60 (d, J=12.2 Hz, 1H); 4.50 (d, J=11.6 Hz, 1H); 3.58-3.53 (m, 1H); 3.50 (q, J=6.4 Hz, 2H); 2.53 (t, J=6.6 Hz, 2H); 2.33 (s, 3H); 1.51-1.37 (m, 2H); 0.99-0.92 (m, 2H); 0.70 (t, J=7.3 Hz, 3H). LCMS1 3.83 min. (M+H)=521. [α]=−126.6° (589 nm, EtOH)

Alternative synthetic schemes for Compound A are included herein as well.

Example 2

1. Preparation of Compound 1

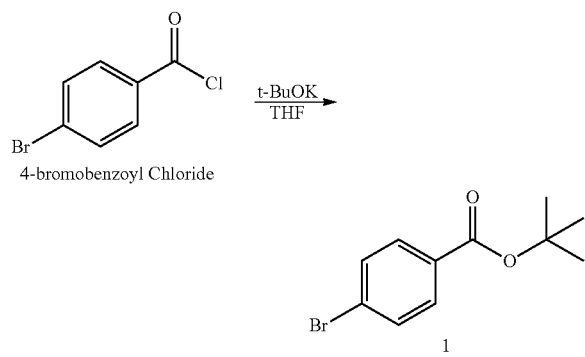

4-bromobenzoyl Chloride

4-Bromobenzoyl chloride (106.0 kg, 482.9 mol) was dissolved in THF (479 L) and cooled to −5~0° C. Potassium tert-butoxide (75.8 kg, 675.5 mol) was dissolved in THF (565 L) to give a hazy solution, which was cooled to −5° C. and added over 5 h to the acid chloride solution via an inline filter so that the temperature was maintained below 5° C.

After 30 minutes, the reaction was assayed for completion by HPLC (<2% starting material). In a separate vessel, NaCl (40 kg) was dissolved in water (736 L), then heptane (886 L) charged and the mixture was cooled to −5° C. The reaction mixture was added over 5 h to the aqueous mixture maintaining below 5° C. The reaction vessel was rinsed with heptane (88 L) and combined with the batch. After layer separation, the aqueous was back-extracted with heptane (294 L). The combined organic layer was washed twice with 426 L water until pH 7, and dried over anhydrous MgSO$_4$ (15.9 kg). The filtrate was concentrated to ~230 L in vacuum at 30-40° C. Charged THF (609 kg) and concentrated to ~230 L. This was repeated until water<0.05% water and <12% heptane.

$^1$H NMR (400 MHz, CDCl$_3$) δ 7.85 (d, J=8.7 Hz, 2H), 7.55 (d, J=8.7 Hz, 2H), 1.60 (s, 3H).
$^{13}$C NMR (100 MHz, CDCl$_3$) δ 165.2, 131.7, 131.2, 131.1, 127.6, 81.7, 28.4.

Anal. Calcd for C$_{11}$H$_{13}$BrO$_2$: C, 51.38; H, 5.10; Br, 31.08. Found: C, 51.61; H, 5.09; Br, 31.35.

2. Preparation of Compound 3

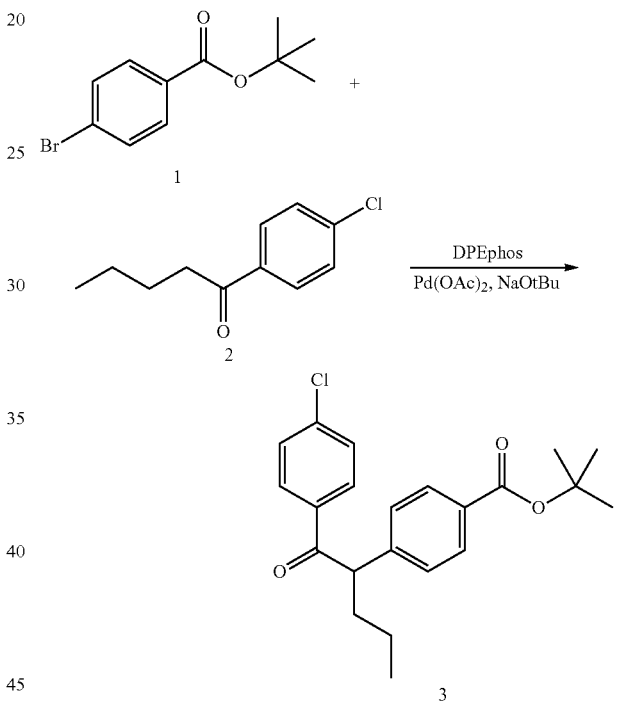

Sodium tert-butoxide (53.0 kg) in THF (404.6 kg) was de-gassed via three N$_2$/vacuum purge cycles and agitated for 15 minutes until the solid was dissolved at 15-20° C. Palladium acetate (454 g), and DPEphos (1081 g) were then charged under nitrogen. The batch was de-gassed again via three N$_2$/vacuum purge cycles and aged for 10 minutes.

4-Chlorovalerophenone (2) (79.0 kg; flushed with THF to remove residual MeOH and H$_2$O until <0.35% water), tert-butyl bromobenzoate 1 (160.7 kg), and THF (66.0 kg) were then added, and the batch was de-gassed again via three N$_2$/vacuum purge cycles. The batch was then heated to 58-64° C. for 8 hours and then checked by HPLC for completion (<2% 3).

After cooling to 15-25° C., the batch was quenched into a 0-5° C. mixture of heptane (730.7 kg) and sodium bicarbonate solution (prepared by dissolving 42.8 kg sodium bicarbonate in 808 L water), keeping at 0-10° C. The reaction vessel was rinsed with heptane (40.5 kg) and combined with the mixture. The mixture was warmed to 15-25° C. and the phases separated.

The aqueous phase was back extracted with heptane (385.0 kg). The combined organics were poured into a pH 8.5 aqueous solution made up with 2-mercaptobenzoic acid (32.0 kg), water (354 kg) and stirred at 25-30° C. for 6-8 h. After layer separation, the organic phase was washed twice with 3% $Na_2CO_3$ solution (549 kg each time). Analysis of the organic layer indicated that the residual 2-mercaptobenzoic was <0.05%. The organic was washed twice with water (426 kg each time) until pH 7, and further washed twice with 20% NaCl solution (476 kg each time).

A silica plug was prepared in the filter using 50 kg silica 60 wet with cold heptane and topped with anhydrous $Na_2SO_4$. The organic batch was then filtered through the silica gel, and washed with heptane (79.1 kg).

The combined filtrates were concentrated to 160 L yellow oil under vacuum at batch temperature<40° C. 2-Propanol (930 kg) was added and the mixture was concentrated to 160 L. Added 2-propanol (620.9 kg) and concentrated to 160 L at <40° C. The oil was diluted with 2-propanol (231 kg), and warmed to 45-60° C. After stirring for 15 min, $H_2O$ (93 kg) was slowly added at 40-60° C. to the slurry, then allowed it to slowly cool to 22° C. The slurry was then cooled to −5-5° C., aged for 2 h, filtered and washed with 50 kg 2:1 2-propanol/water.

The wet cake was dried under vacuum at 38-40° C./22 in. $Hg/N_2$ for 22 h to yield product 2 as an off-white solid.

$^1$HNMR (400 MHz, $CDCl_3$) δ 7.92 (m, 2H), 7.87 (m, 2H), 7.36 (m, 2H), 7.33 (m, 2H), 4.54 (t, J=7.2 Hz, 1H), 2.16 (m, 1H), 1.83 (m, 1H), 1.57 (s, 9H), 1.37-1.17 (m, 2H), 0.92 (t, J=7.3 Hz, 3H).

$^{13}$C NMR (100 MHz, $CDCl_3$) δ 198.4, 165.6, 144.3, 139.6, 135.2, 131.2, 130.3, 130.2, 129.1, 128.3, 81.2, 53.7, 36.0, 28.4, 20.9, 14.2.

Anal. Calcd for $C_{22}H_{25}ClO_3$: C, 70.86; H, 6.76; Cl, 9.51. Found: C, 70.73; H, 6.98; Cl, 9.21.

HPLC conditions: Zorbax Eclipse XDB-C8, 4.6×150 mm; A: 0.1% $H_3PO_4$ aqueous; B: acetonitrile; 70% to 95% B over 15 min, hold 2 min, post time 4 min. 1.0 mL/min, 10 μL, 210 nm, 30° C. column temperature; p-chlorovalerophenone, RT=4.36 min; tert-butyl 4-bromobenzoate, RT=5.56 min; product, RT=9.74 min; product acid, RT=3.26 min.

Note: The catalyst used above can be replaced with BINAP or tol-BINAP.

3. Preparation of Compound 4

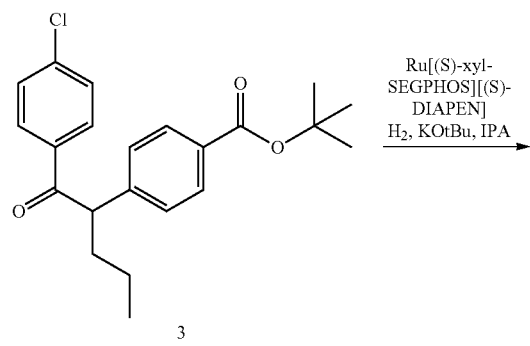

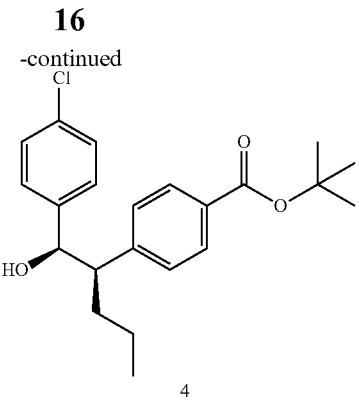

Ketone 3 (110 kg) in IPA (682 kg) was charged to the hydrogenation vessel, and the solution was thoroughly degassed using $N_2$/vacuum purge cycles.

The catalyst solution was prepared in a separate vessel: potassium tert-butoxide (7.0 kg) was dissolved in IPA (66 kg) and thoroughly purged with $N_2$. The catalyst Ru[(S)-XYL-SEGPHOS][(S)-DIAPEN] (551 g) was added, the catalyst mixture aged for 1 hour at 25-30° C., whilst purging with $N_2$. This catalyst preparation was then added to the ketone IPA solution, taking care to exclude air during this operation, and de-gassing using $N_2$/vacuum purge cycles after the addition. The batch was then hydrogenated for 3-5 hours at 20-25° C. using a $H_2$ pressure of 0.64-0.68 Mpa.

The reaction solution was passed through silica gel column (46.4 kg) two times. The filtrate was concentrated to ~880 L by distillation at <40° C. The solution was then heated to 55-58° C., and slowly added water (780 kg) over 1.5 h at the same temperatures. After stirring for 1-1.5 h, the mixture was cooled to 20-25° C. over 2-3 h. The slurry was aged for 2-3 h, then cooled to 0-5° C. over 2-3 h. After stirring for 1-2 h, the slurry was filtered, and the cake was washed twice with cold 2:1 IPA:water (230 kg).

The wet cake was dried in 40-45° C. vacuum for 28-30 h, to give the product 4 as an off-white solid.

$^1$H NMR (400 MHz, $CDCl_3$) δ 7.96 (m, 2H), 7.32 (m, 2H), 7.26 (m, 2H), 7.22 (m, 2H), 4.76 (dd, J=7.7, 2.9 Hz, 1H), 2.89 (ddd, J=11.5, 7.7, 4.2 Hz, 1H), 1.84 (d, J=2.9 Hz, —OH), 1.62 (s, 9H), 1.61 (m, 1H), 1.41 (m, 1H), 1.05 (m, 2H), 0.76 (t, J=7.3 Hz, 3H).

$^{13}$C NMR (100 MHz, $CDCl_3$) δ 165.9, 146.3, 141.4, 133.7, 131.0, 129.8, 128.9, 128.7, 128.4, 81.1, 78.01, 54.2, 34.2, 28.4, 20.6, 14.1.

Anal. Calcd for $C_{22}H_{27}ClO_3$: C, 70.48; H, 7.26; Cl, 9.46. Found, C, 70.45; H, 7.40; Cl, 9.24.

Zorbax Eclipse XDB-C8, 4.6×150 mm; A: 0.1% $H_3PO_4$ aqueous; B: acetonitrile; 70% to 95% B over 15 min, hold 2 min, post time 4 min. 1.0 mL/min, 10 μL, 210 nm, 30° C. column temperature; Major diastereomer, RT=7.74 min; minor diastereomer, RT=6.89 min; Major diastereomer acid, RT=2.66 min; minor diastereomer acid, RT=2.27 min.

Chiral SFC Method: Chiralpak AD-H (250×4 6 mm), isocratic 15% $MeOH/CO_2$, 1.5 mL/min, 200 bar, 35° C., 215 nm, 15 min: desired alcohol, RT=9.8 min; enantiomeric alcohol, RT=10.6 min.; diastereomeric alcohols: 5.2 & 6.3 min.

4. Preparation of Compound 5

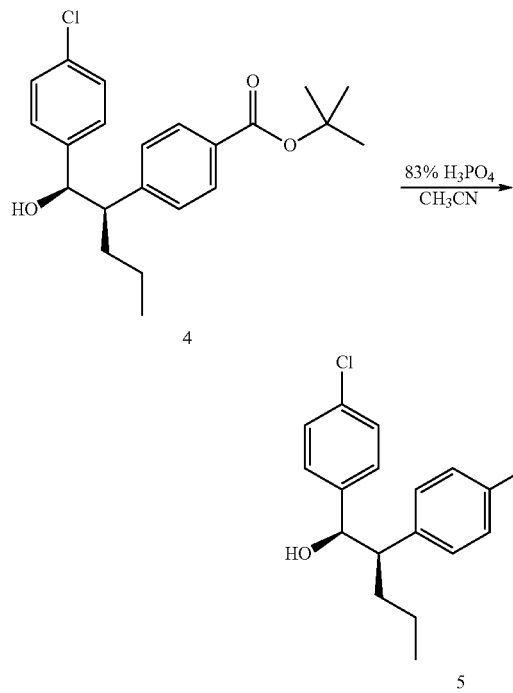

Alcohol 4 (90 kg) was slurried in acetonitrile (600 kg) and orthophosphoric acid (85 wt %, 113.6 kg) charged followed by 60 kg acetonitrile for chasing orthophosphoric acid. The slurry was inerted with $N_2$ and heated to 62-68° C., monitoring hourly for conversion.

After 3.5-4 h, reaction was complete by HPLC. The solution was cooled to 55-65° C. and water (98 kg) charged over 45 minutes to effect crystallization. The mixture was cooled to 45-50° C., and seeded with 430 g compound 5 to effect crystallization if crystallization has not occurred. Once a seedbed was established at 45-50° C., further water (861 kg) was charged, and stirred for 1-2 h at these temperatures. The slurry was cooled slowly to 20-25° C., and then aged for 2-3 h. The product was filtered and washed with 88 kg of 3:1 $H_2O/CH_3CN$.

The wet cake was dried under vacuum at 38-40° C. for 10-16 h to afford product 5 as a yellow solid as a monohydrate.

$^1$H NMR (400 MHz, DMSO-$d_6$) δ 12.71 (br s, —$CO_2H$), 7.79 (d, J=8.3 Hz, 2H), 7.29 (d, J=8.4 Hz, 2H), 7.19-7.25 (m, 4H), 5.32 (br s, —OH), 4.76 (d, J=6.3 Hz, 1H), 2.85 (dt, J=10.7, 5.4 Hz, 1H), 1.61 (m, 1H), 1.44 (m, 1H), 1.00 (m, 2H), 0.73 (t, J=7.3 Hz, 3H).

$^{13}$C NMR (100 MHz, DMSO-$d_6$) δ 167.4, 147.7, 143.7, 131.0, 129.1, 128.6, 128.4, 128.3, 127.6, 75.1, 52.7, 34.0, 20.0, 13.8.

Anal. Calcd for $C_{18}H_{19}ClO_3 \cdot H_2O$: C, 64.19; H, 6.28; Cl, 10.53. Found: C, 64.43; H, 6.06; Cl, 10.30.

Zorbax Eclipse Plus C18, 4.6×50 mm; A: 0.1% $H_3PO_4$ aqueous; B: acetonitrile; 75% to 95% B over 4 min, hold 1 min, post time 2 min. 1.5 mL/min, 3 μL, 210 nm, 22° C. column temperature; starting material, RT=2.49 min; product, RT=0.65 min.

Chiral HPLC Method: ChiralPak IB (250×4.6 mm), 0.1% TFA in heptane, B=0.1% TFA in 50/50 EtOH/MeOH, isocratic 6% B, 1.0 mL/min, 10 μL of 1.5 mg/mL EtOH, 25° C., 254 nm, 30 min: major enantiomer, RT=17.10 min; minor enantiomer, RT=21.22 min.

5. 2-Bromo-6-fluoro-4-methylaniline 7

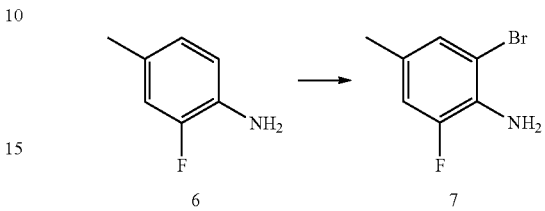

6-fluoro-4-methylaniline 6 (15 kg) was added to a mixture of MTBE (92 L, 66.6 kg) calcium carbonate (12 kg) and water (135 kg), inerted and cooled to <5° C. Bromine (18.22 kg) was charged, keeping T<10° C. Age for 30 minutes at T<10° C. The batch was warmed to ~18° C. and allowed to settle.

The lower aqueous layer was cut away and the organics washed with 5% aq sodium metabisulfite (75 L) then water (75 L). The organic phase was solvent-switched to toluene (at <40° C. using vacuum), final volume 45-60 L, then passed through a silica pad (15 kg) in an oyster filter, washing with toluene (60 L, 52 kg). The filtrates were combined and reduced by vacuum distillation (T<40° C.).

6. 7-Fluoro-5-methyl-1H-indole 8

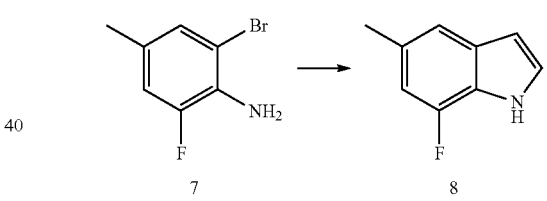

Method 1:

Palladium allyl chloride dimer (0.74 kg) and DPE Phos (2.17 kg) were slurried in heptane (165 L, 113 kg) and degassed using $N_2$/vacuum cycles. Dicyclohexylamine (7.85 kg) was added, de-gassed again using $N_2$/vacuum cycles, and the resulting suspension was aged for no more than 40 minutes.

In another vessel, the bromoaniline 7 (16.5 kg as a 20 wt % toluene solution), dicyclohexylmethylamine (36.2 kg) and trimethylsilyl acetylene (15.1 kg) were de-gassed using $N_2$/vacuum cycles. The catalyst suspension was then transferred into this vessel over 5 minutes, and the vessel was pressurised to 2300 mbar and heated to 70° C. overnight.

After 17 hours, HPLC analysis showed no starting material present. The batch was cooled to 20° C. and filtered through ~3 kg Solka-Floc in an oyster filter. Heptane (30 L) was used to rinse the vessel then wash the filter cake. The filtrate and wash were combined and washed with HCl (made up with 15.4 kg conc. HCl and 75 kg water), then water (80 kg).

50 kg silica was loaded into the large oyster filter and wetted with cold heptane (100 L). The organics were then filtered through the silica, washing/eluting with toluene/heptane (21 kg/38 kg) then toluene (55 kg). The filtrate fractions were combined and distilled to a volume of 90 L under reduced pressure with maximum batch temperature of 50° C.

Tetrabutylammonium fluoride trihydrate (27.8 kg) was dissolved in THF (79 kg) and methanol (4.1 L), and the indole toluene solution added to it over 5 minutes. The solution was heated to 80-85° C. and THF removed by atmospheric distillation.

Once reaction was complete, distillation was continued at 100-150 mbar to remove residual THF. The batch was then cooled to 20° C. and washed with 5 wt % brine (44 kg). The brine wash was extracted with toluene (42 kg). The combined toluene organics were then washed with 5 wt % brine. The organics were filtered and the filtrate concentrated to give a toluene solution of indole 8.

$^1$H NMR (400 MHz, CDCl$_3$) δ 8.20 (br s, —NH), 7.22 (d, J=0.6 Hz, 1H), 7.20 (dd, J=2.9, 2.7 Hz, 1H), 6.78 (dd, J=12.0, 0.7 Hz, 1H), 6.52 (ddd, J=3.3, 3.3, 2.2 Hz, 1H), 2.46 (s, 3H).

$^{13}$C NMR (100 MHz, CDCl$_3$) δ 149.4 (d, J=242.9 Hz), 131.8 (d, J=5.5 Hz), 130.2 (d, J=5.7 Hz), 125.0, 122.6 (d, J=13.2 Hz), 116.1 (d, J=3.1 Hz), 108.6 (d, J=15.7 Hz), 103.0 (d, J=2.3 Hz), 21.6.

$^{19}$F NMR (376 MHz, CDCl$_3$) δ −136.5.

Anal. Calcd for C$_9$H$_8$FN: C, 72.47; H, 5.41; F, 12.74; N, 9.39. Found: C, 72.15; H, 5.34; F, 12.74; N, 9.28.

Zorbax Eclipse XDB-C8, 4.6×150 mm; A: 0.1% H$_3$PO$_4$ aqueous; B: acetonitrile; 70% to 95% B over 15 min, hold 2 min, post time 4 min. 1.0 mL/min, 10 μL, 210 nm, 30° C. column temperature; product, RT=2.67 min.

Method 2:
Step 1: Sugasawa Reaction

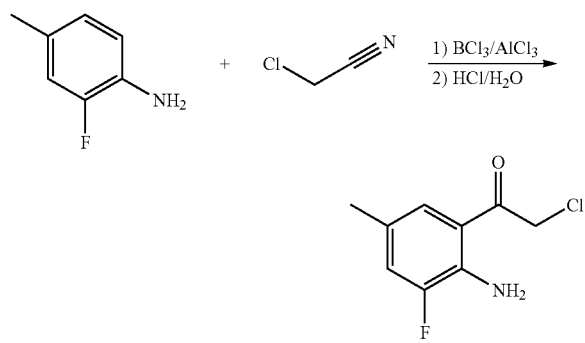

| Reagent | MW | Amount | mmol | Equiv. |
| --- | --- | --- | --- | --- |
| 2-Fluoro-4-methylaniline | 125.15 | 12.52 g | 100 | 2.00 |
| Chloroacetonitrile | 75.5 | 3.78 g | 50 | 1.00 |
| BCl$_3$/CH$_2$Cl$_2$ (1.0M) | | 110 mL | 110 | 2.20 |
| AlCl$_3$ pellet | 133.34 | 8.00 g | 60 | 1.20 |
| 1,2-Dichloroethane (DCE) | | 125 mL | | 10 V of aniline |
| HCl (2.0M in water) | | 80 mL | 160 | |
| Product-chloroacetophenone | 201.63 | 10.08 g | 50 | 100% |

A vessel was cooled via ice bath, was charged with AlCl$_3$ pellets, 100 mL DCE, and BCl$_3$/DCM solution 110 mL under N$_2$ with an outlet into an aqueous NaOH solution bath. A solution of SM-aniline was then added dropwise with caution to keep t<20 C. Upon completion, the grey slurry was added SM-nitrile in one portion, and extra DCE was used to rinse the RBF. The ice bath was removed, and the reaction was heated to reflux.

After 6 h of reflux, the mixture was cooled, quenched with 2N HCl 80 mL, and heated to reflux for 20 min. The mixture was extracted with DCM, washed with 2N HCl, water, and brine. After concentration, the solid was stirred with 25 mL hexanes, cooled via an ice bath, filtered, and washed with extra 50 mL hexanes, A dark yellow solid was obtained.

The combined HCl wash was treated with NaOH (pellets, 14.7 g) to pH=5-6, extracted with MTBE/Heptane (1:1) and concentrated.

Step 2: Reduction and Cyclization

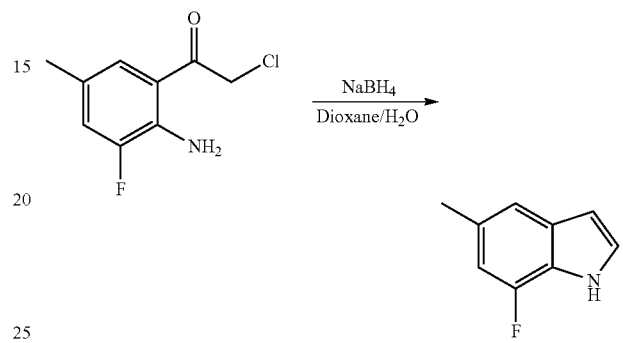

| Reagent | MW | Amount | mmol | Equiv. |
| --- | --- | --- | --- | --- |
| chloroacetophenone (96.6%) | 201.63 | 2033 mg | 9.74 | 1.00 |
| NaBH$_4$ | 37.83 | 456 mg | 12.0 | 2.46 |
| 1,4-Dioxane | | 20 mL | | 10 V |
| Water | | 2.0 mL | | 1 V |
| Product-indole | 149.16 | 1453 mg | 9.74 | 100% |

Chloroacetophenone was dissolved in dioxane followed by addition of NaBH$_4$ and water. The mixture was aged at room temperature for 25 min before heated to reflux for 2 h, cooled to room temperature, worked up with MTBE and water. Concentration of the workup gave a brown clear liquid, which solidified upon freezing.

The formed indole was used to prepare nosyl indole as a white solid powder after recrystallization from MeCN/water (2:1).

7. 7-Fluoro-5-methyl-1-[(4-nitrophenyl)sulfonyl]-1H-indole 8

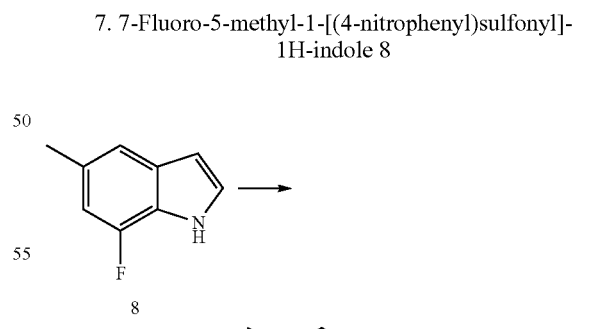

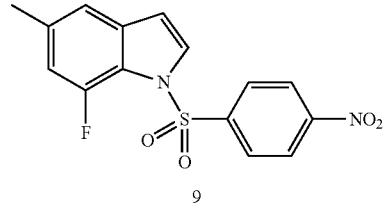

Indole 8 (3.2 kg as a 10 wt % solution in toluene) was distilled to a volume of 90 L under reduced pressure with a maximum batch temperature of 50° C. 48 wt % sodium hydroxide (15 kg, 9.6 L) was charged. The batch was cooled to 15° C. and tetrabutylammonium sulphate (363 g) added. Nosyl chloride (5.92 kg) was dissolved in toluene (15.6 kg) and the solution charged slowly, keeping T<25° C. After 10 minutes, HPLC analysis showed complete reaction.

Cold (10° C.) 5 wt % sodium hydrogen carbonate solution (45 L) was charged and the phases separated. The organics were washed with 5 wt % sodium hydrogen carbonate solution (31 L), and then washed with HCl (30 kg water & 730 mL conc HCl). The organics were distilled to a volume of ~45 L under reduced pressure with maximum batch temperature of 40° C. Isopropanol (35 kg, 45 L) was added, and the solution passed through the CUNO carbon filtration system, using a 3.5 kg R-55SLP cartridge.

Isopropanol (19.3 kg, 25 L) was added to the filtrate and it was distilled under reduced pressure with maximum batch temperature of 40° C., adding additional isopropanol until <10 mol % toluene is present by NMR, to a final volume of ~10 wt % product in IPA. The batch was cooled to 5° C. to crystallise the product. The slurry was filtered, and washed with isopropanol (30 L, 24 kg), then cold IPA/water (24 kg/1.5 kg). The solid was dried on the filter under a nitrogen stream to give the product 9 as a brown solid.

$^1$H NMR (400 MHz, CDCl$_3$) δ 8.32 (d, J=8.8 Hz, 1H), 8.11 (d, J=8.8 Hz, 1H), 7.70 (d, J=3.7 Hz, 1H), 7.13, (s, 1H), 6.81 (d, J=13.1 Hz, 1H), 6.66 (dd, J=3.5, 2.4 Hz, 1H), 2.38 (s, 3H);).

$^{13}$C NMR (100 MHz, CDCl$_3$) δ 150.8, 149.2 (d, J=249.2 Hz), 144.1, 135.5 (d, J=6.5 Hz), 135.3 (d, J=3.8 Hz), 129.2 (d, J=2.8 Hz), 128.7, 128.6, 120.0 (d, J=11.2 Hz), 117.6 (J=3.4 Hz), 113.1 (d, J=19.4 Hz), 109.1 (d, J=2.1 Hz).

Anal. Calcd for C$_{15}$H$_{11}$FN$_2$O$_4$S: C, 53.89; H, 3.32; F, 5.68; N, 8.38; 0, 19.14; S, 9.59. Found: C, 53.68; H, 3.16; F, 5.58; N, 8.30; S, 9.64.

Zorbax Eclipse XDB-C8, 4.6×150 mm; A: 0.1% H$_3$PO$_4$ aqueous; B: acetonitrile; 70% to 95% B over 15 min, hold 2 min, post time 4 min. 1.0 mL/min, 10 μL, 210 nm, 30° C. column temperature; starting indole, RT=2.49 min; N-(4-nosyl)-indole, RT=3.74 min.

8. 4-[(1S)-1-((R)-(4-Chlorophenyl){7-fluoro-5-methyl-1-[(4-nitrophenyl)sulfonyl]-1H-indol-3-yl}methyl)butyl]benzoic acid 10

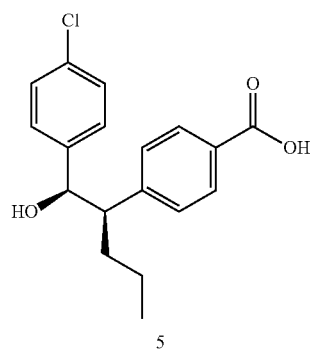

5

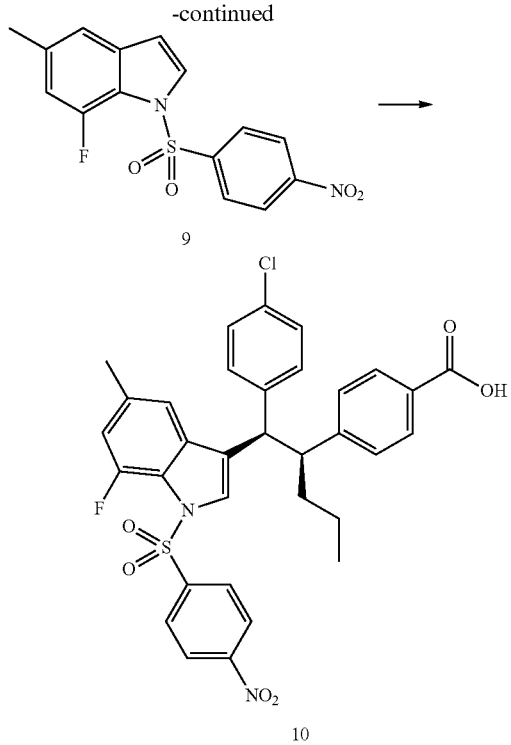

Method 1:

Acid 5 (8.2 kg of 98 wt %) and nosyl indole 9 (8.86 kg, 96 wt %) were slurried in dichloromethane (160 kg), inerted and cooled to 15° C. BF$_3$OEt$_2$ (10.74 kg) was charged, keeping T<25° C. The brown solution was aged at 20° C. for 18 h, then cooled to 15° C. and water (80 kg) added.

The biphasic mixture was filtered through a pad of Solka-Floc (~5 kg) contained in an oyster filter, and the pad was washed with 10 kg dichloromethane. The filtrate was separated and the lower DCM organic washed with water (80 kg).

The DCM organics were then stirred gently overnight with MP-TMT resin (2.4 kg), then filtered, washing with IPAC (30 L).

The filtrate volume was then reduced by vacuum distillation (T<35° C.). Isopropyl acetate (105 kg) was added, and this solution was filtered, washing with IPAC and DCM.

The IPAC solution was warmed to 50° C. and heptane (38 kg) charged, keeping T at approximately 45° C. Seed (10 g) was charged, and the batch cooled to 20° C. overnight (using a linear ramp on the PCS system). Further seeding or heptane addition caused crystallisation.

The product was dried in vacuo to give 9 as a tan solid.
Method 2:

To a mixture of alcohol 5 (42.7 kg, 93.7 wt %) and indole 9 (41.3 kg, 99.5 wt %) was added trifluoroacetic acid (943 kg) and methanesulfonic acid (6.0 kg). After stirring for 19 h at 22° C., the solution was diluted with isopropyl acetate (1070 kg) (temperature controlled from 10-25° C.), cold 20 wt % NaOH (1200 kg), and 15 wt % K$_2$HPO$_4$ (1430 kg). After separating the layers, the organic was pH adjusted to a pH of 2 with 0.1 N HCl (136 kg). After separating the layers, the organic was washed with water (1207 kg).

The organic phase was filtered and then washed with IPAC. The organic phase was concentrated and flushed with IPAC to remove water (target: <200 ug/mL).

The batch was seeded with 0.5 wt % (relative to products) at 35° C. and aged for 60 min, then cooled 20° C. over 1 h to allow a seed bed to develop. Heptane was added over 300 min. The slurry was filtered, washed with 1:4 IPAC/heptane (430 kg), and vacuum dried at 40° C. overnight to afford product 10 as a tan solid.

4-[(1S)-1-((R)-(4-chlorophenyl){7-fluoro-5-methyl-1-[(4-nitrophenyl)sulfonyl]-1H-indol-3-yl}methyl)butyl]benzoic acid-isopropyl acetate (1:1)

Major Diastereomer:

$^1$H NMR (400 MHz, CDCl$_3$) δ 8.13 (d, J=8.9 Hz, 2H), 8.05 (d, J=8.3 Hz, 2H), 7.52 (d, J=8.7 Hz, 2H), 7.45 (s, 1H), 7.40 (d, J=8.3 Hz, 2H), 7.38-7.31 (m, 4H), 6.89 (s, 1H), 6.68 (d, J=12.8 Hz, 1H), 4.32 (d, J=11.5 Hz, 1H), 3.43 (dt, J=10.8, 3.5 Hz, 1H), 3.29 (s, 3H), 1.55 (m, 1H), 1.47 (m, 1H), 1.06 (m, 2H), 0.76 (t, J=7.3 Hz, 3H).

$^{13}$C NMR (100 MHz, CDCl$_3$) δ 171.4, 151.0, 150.7, 149.1 (d, J=250.6 Hz), 143.4, 140.1, 135.4 (d, J=6.4 Hz), 134.9 (d, J=3.2 Hz), 133.1, 130.7, 129.9, 129.3, 128.6, 128.5, 127.7, 127.7, 126.4 (d, J=3.2 Hz), 124.5, 124.4, 119.8 (d, J=11.1 Hz), 115.5, 113.5 (d, J=19.3 Hz), 50.5, 47.7, 37.4, 21.4, 20.4, 14.1.

$^1$H NMR (400 MHz, DMSO-d$_6$) δ 8.23 (d, J=8.8 Hz, 2H), 7.95 (s, 1H), 7.83 (d, J=8.2 Hz, 2H), 7.70-7.60 (m, 4H), 7.57 (d, J=8.2 Hz, 2H), 7.39 (d, J=8.4 Hz, 2H), 7.27 (s, 1H), 6.83 (d, J=13.2 Hz, 1H), 4.61 (d, J=11.8 Hz, 1H), 3.80 (dt, J=11.6, 3.2 Hz, 1H), 2.25 (s, 3H), 1.45 (m, 1H), 1.29 (m, 1H), 0.93 (m, 2H), 0.68 (t, J=7.3 Hz, 3H).

$^{13}$C NMR (100 MHz, DMSO-d$_6$) δ 171.8, 167.2, 150.4, 149.9, 148.2 (d, J=250.0 Hz), 141.7 (d, J=30.3 Hz), 135.0 (d, J=6.5 Hz), 134.8 (d, J=3.2 Hz), 131.1, 130.2, 129.1, 128.5, 128.4, 128.3, 128.1, 126.8, 125.5 (d, J=1.6 Hz), 124.7, 118.5 (d, J=10.3 Hz), 115.7, 112.7 (d, J=19.5 Hz), 47.9, 45.8, 36.7, 20.6, 19.7, 13.6.

$^{19}$F NMR (376 MHz, CDCl$_3$) δ −122.8.

Anal. Calcd for C$_{38}$H$_{38}$ClFN$_2$O$_8$S: C, 61.91; H, 5.20; Cl, 4.81; F, 2.58; N, 3.80; S, 4.35. Found: C, 62.04; H, 5.09; N, 3.79; Cl, 4.82; F, 2.63; S, 4.47.

Minor Diastereomer:

Selective NMR signals: $^1$H NMR (400 MHz, CDCl$_3$) δ 8.32 (d, J=8.9 Hz, 2H), 8.08 (d, J=8.9 Hz, 2H), 7.94 (d, J=8.2 Hz, 2H), 7.72 (s, 1H), 7.16 (d, J=8.2 Hz, 2H), 7.07 (s, 1H), 7.05 (d, J=8.5 Hz, 2H), 6.98 (d, J=8.5 Hz, 2H), 6.68 (d, J=12.8 Hz, 1H), 4.27 (d, J=10.8 Hz, 1H), 3.47 (m, 1H), 2.37 (s, 3H), 1.85 (m, 1H), 1.20 (m, 1H), 1.15 (m, 2H), 0.83 (t, J=7.3 Hz, 3H); $^{19}$F NMR (376 MHz, CDCl$_3$) δ −122.3; Anal. Calcd for C$_{33}$H$_{28}$ClFN$_2$O$_6$S.0.5 MTBE.0.2 heptane: C, 63.38; H, 5.36; N, 4.01; Cl, 5.07; F, 2.72; S, 4.59. Found: C, 63.59; H, 5.36; N, 3.84; Cl, 4.94; F, 2.75; S, 4.61.

Zorbax Eclipse XDB-C8, 4.6×150 mm; A: 0.1% H$_3$PO$_4$ aqueous; B: acetonitrile; 70% to 95% B over 15 min, hold 2 min, post time 4 min. 1.0 mL/min, 10 μL, 210 nm, 30° C. column temperature; Major diastereomer, RT=7.23 min; minor diastereomer, RT=5.66 min; 3-tert-butylated indole 5, RT=6.69 min.

Chiral SFC Method: ChiralPak IB column (250×4.6 mm), isocratic 25% MeOH w 0.1% TFA/CO2, 1.5 ml/min, 200 bar, 35 C, 35 min; Enantiomer of desired (R,S), RT=17.28; Desired (S,R), RT=18.11 min; Diastereomer of desired (S,S), RT=19.85 min; Enantiomer of diastereomer of desired (R,R), RT=24.15 min.

9. 3-[(4-{(1S)-1-[(R)-(4-chlorophenyl)(7-fluoro-5-methyl indol-3-yl)methyl]butyl}benzoyl)amino]-propanoic acid 12

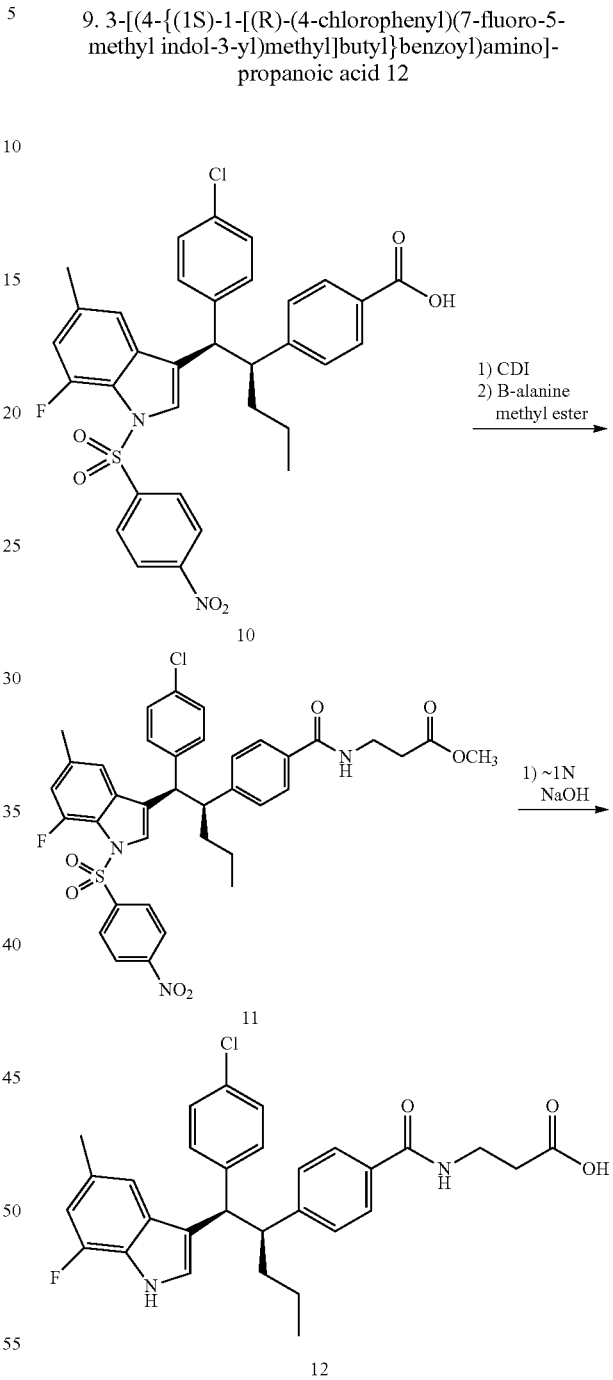

Penultimate compound 10 (7.40 kg) was dissolved in THF (32.9 kg) and degassed using N$_2$/vacuum purge cycles. N,N-carbonyldiimidazole (2.64 kg) was charged, and the batch was warmed to 40° C. for 45 minutes. HPLC showed complete conversion to acylimidazolide.

The batch was cooled to 30° C. and β-alanine methyl ester (2.60 kg) added. The batch was then heated to 60° C. for 4 hours. HPLC analysis showed complete conversion to amide/ester.

2.5 M NaOH (32.6 L; prepared from 5.70 kg 10 M NaOH and 24.5 kg water) was charged and the batch aged at 60° C. for 1.5 h, then further 10 M NaOH (1.63 kg) added and the batch aged at 60° C. overnight. The batch was cooled to 25° C. and the lower aqueous layer cut away. Further water (14.1 kg) and 10 M NaOH (2.78 kg) were charged, and the batch heated to 60° C. for 2 hours.

The batch was cooled to 25° C. and MTBE (48.8 L, 36.1 kg) charged, then 5 wt % NaCl (2.44 kg NaCl in 48.8 kg water). After agitation and settling, the phases were separated and the organics washed with 5 wt % NaCl (2.44 kg NaCl in 48.8 kg water), 3 M HCl (2.68 kg conc. HCl in 9.8 kg water) and water (48.8 kg).

The organics were concentrated to a volume of 15 L using vacuum with a maximum batch temperature of 30° C. Isopropanol (47.4 L, 37.2 kg) was then added and the batch concentrated to 15 L again. Isopropanol (27 L, 21 kg) was added and the solution was filtered, washing with isopropanol. The filtrate was then vacuum distilled with maximum batch temperature of 30° C. Water (26.6 kg) was added, seed added and the slurry aged for 45 minutes.

The slurry was filtered, washing with IPA/water (4.6 kg/11.8 kg) then water (35 kg). The solid was dried.

The cake was transferred to a vacuum oven at 42° C. for 24 h. The dried solids were passed through a co-mill to give product 12 (98.7 LCAP, 101 LCWP) as an off-white solid.

Amorphous Material

Figure 16:
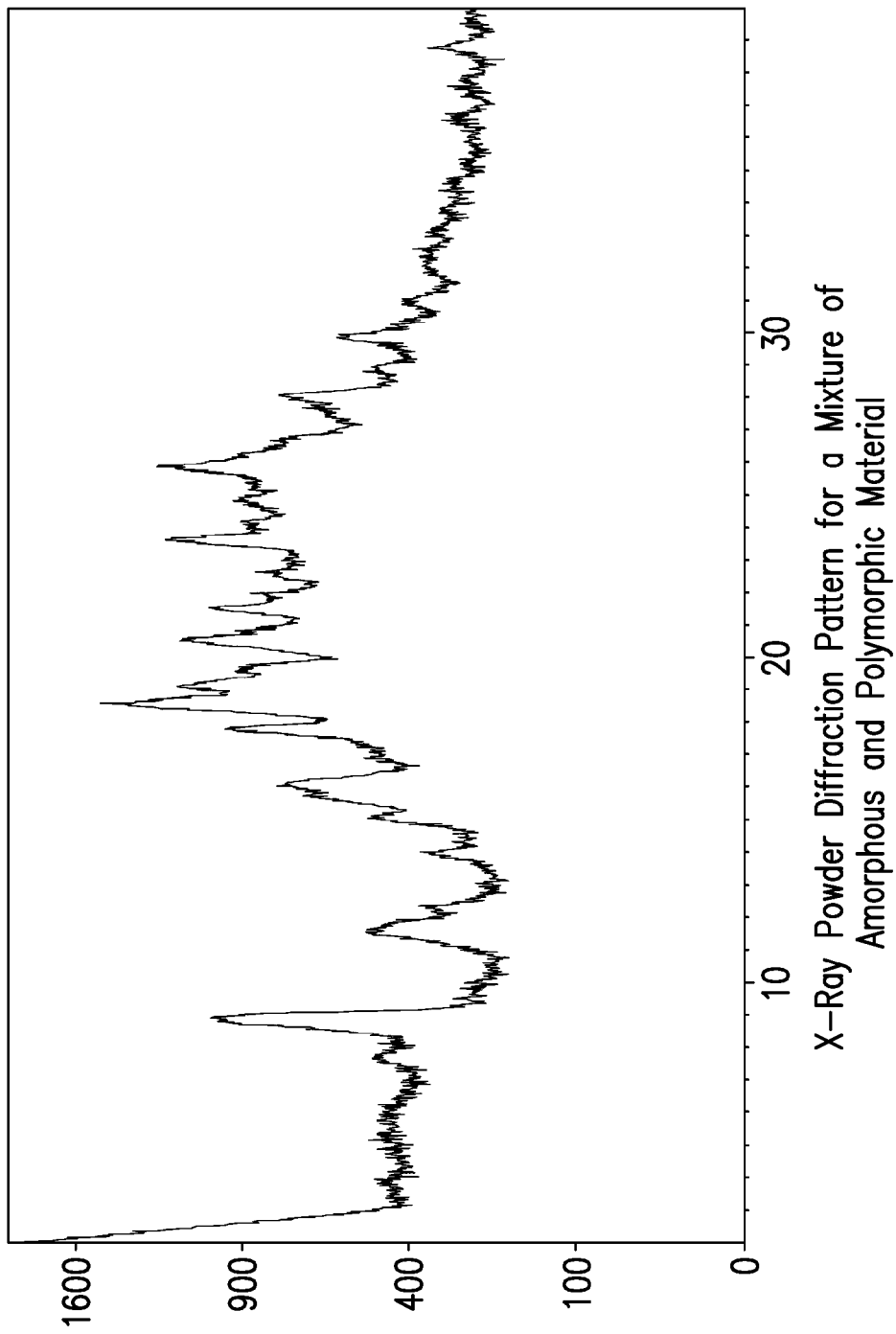
FIG. 16 is an X Ray Powder Diffraction pattern for comparison purposes of Compound A containing a mixture of amorphous product and polymorphs.

The amorphous phase of compound A was obtained by lyophilization. It can also be obtained by other techniques such as spraying drying and melt quenching. Amorphous material can be detected in samples as shown in FIG. 16, as part of a mixture of amorphous and polymorphic materials.

Polymorphic Materials

The polymorphic forms of compound A were prepared using material that was produced as described in steps 1 through 9. Seed crystal was obtained from lab scale preparations spontaneously or upon chromatographic purification. An X Ray Powder Diffraction Pattern of a mixture of amorphous and polymorphic forms is included for comparison purposes as FIG. 16.

X-ray powder diffraction (XRPD) patterns for the solid phases of compound A were generated on a Philips Analytical X'Pert PRO X-ray Diffraction System with PW3040/60 console. The diffraction peak positions were referenced by silicon which has a 2 theta value of 28.443 degree. A PW3373/00 ceramic Cu LEF X-ray tube K-Alpha radiation was used as the source. The experiments were run at ambient condition except for the anhydrate of polymorphic form I, where the measurement was carried out at 5% relative humidity at room temperature.

Solid-state carbon-13 NMR spectra were obtained on a Bruker DSX 400WB NMR system using a Bruker 4 mm double resonance CPMAS probe. The carbon-13 NMR spectrum utilized proton/carbon-13 cross-polarization magic-angle spinning with variable-amplitude cross polarization. The sample was spun at 8 kHz. Chemical shifts are reported on the TMS scale using the carbonyl carbon of glycine (176.03 p.p.m.) as a secondary reference.

Solid-state fluorine-19 NMR spectra were obtained on a Bruker DSX 500WB NMR system using a Bruker 4 mm CRAMPS probe. The NMR spectrum utilized proton/fluorine-19 cross-polarization magic-angle spinning with variable-amplitude cross polarization. The samples were spun at 15.0 kHz. A vespel endcap was utilized to minimize fluorine background. Chemical shifts are reported using poly(tetrafluoroethylene) (Teflon) as an external secondary reference which was assigned a chemical shift of −122 ppm.

Differential Scanning Calorimetry

TA Instruments DSC 2910 or equivalent instrumentation is used to conduct differential scanning calorimetry. Between 1 and 5 mg of a sample is weighed into a sample pan and placed at the sample position in the calorimeter cell. An empty pan is placed at the reference position (either the sample and reference pans are closed or both are open). The calorimeter cell is closed and a flow of nitrogen is passed through the cell. The heating program is set to heat the sample at a heating rate of 10° C./min to a temperature of ~300° C. The heating program is started. At the completion of the run, the data are analyzed using the Universal analysis program contained in the system software. Integration of any endotherms present is carried out between points on the baseline at temperatures above and below the range in which the endothermic event(s) are observed. Reported data include observed onset temperature, peak temperature, and associated enthalpy of melting.

Thermogravimetric Analysis (TG):

An instrument such as Perkin Elmer model TGA 7 or equivalent is used to conduct thermogravimetric analysis. Experiments are performed under a flow of nitrogen at a heating rate of 10° C./min, and samples are heated to a temperature of about 300° C. To start an experiment, the balance is tared, approximately 3 to 20 mg of sample is added to the platinum pan, the furnace is raised, the sample is weighed, and the heating program is started. Weight/temperature data are collected automatically by the instrument and can be converted to weight percent/temperature. Analysis of the results is carried out by selecting the Delta Y function within the instrument software and the weight loss up to the completion of melting is reported.

Hydrate

The hydrate was produced in accordance with the process set forth above. The term hydrate refers to different crystalline forms of the compound, such as the monohydrate, dihydrate, hemi-hydrate, and the like.

Hydrate: $^1$H NMR (400 MHz, CDCl$_3$) δ 8.20 (br s, NH), 7.46 (d, J=8.1 Hz, 2H), 7.28 (d, J=8.5 Hz, 2H), 7.25 (d, J=8.5 Hz, 2H), 7.17 (d, J=8.1 Hz, 2H), 6.94 (s, 1H), 6.83 (d, J=2.1 Hz, 1H), 6.72 (t, J=6.0 Hz, —CONH), 6.60 (d, J=11.9 Hz, 1H), 4.37 (d, J=10.7 Hz, 1H), 3.58 (m, 2H), 3.37 (dt, J=10.7, 3.2 Hz, 1H), 2.57 (m, 2H), 2.35 (s, 3H), 1.50 (m, 1H), 1.40 (m, 1H), 0.98 (m, 2H), 0.71 (t, J=7.3 Hz, 3H).

$^{13}$C NMR (100 MHz, CDCl$_3$) δ 176.6, 168.2, 149.2 (d, $J_{CF}$=243.8 Hz), 149.0, 142.6, 132.1, 131.7, 130.9 (d, $J_{CF}$=5.5 Hz), 130.0, 129.6 (d, $J_{CF}$=5.6 Hz), 128.8, 128.5, 127.1, 122.8, 122.6 (d, $J_{CF}$=13.3 Hz), 118.6 (d, $J_{CF}$=1.2 Hz), 114.3 (d, $J_{CF}$=2.5 Hz), 108.6 (d, $J_{CF}$=15.7 Hz), 50.3, 48.2, 37.3, 35.5, 34.0, 21.8, 20.5, 14.1.

$^{19}$F NMR (376 MHz, CDCl$_3$) δ −136.3.

Anal. Calcd for $C_{30}H_{31}ClFN_2O_{3.5}$: C, 67.98; H, 5.90; Cl, 6.69; F, 3.58; N, 5.29. Found: C, 68.11; H, 5.84; Cl, 6.70; F, 3.54; N, 5.33.

Zorbax Eclipse XDB-C8, 4.6×150 mm; A: 0.1% $H_3PO_4$ aqueous; B: acetonitrile; 70% to 95% B over 15 min, hold 2 min, post time 4 min. 1.0 mL/min, 10 μL, 210 nm, 30° C. column temperature; desired, RT=3.65 min.

Chiral SFC LC: Chiralpak AD-H column (250×4 6 mm), isocratic 15% MeOH with 25 mM isobutylamine/CO2, 1.5 mL/min, 200 bar, 35° C., 210 nm, 30 min run time: Desired, RT=18.9 min; enantiomer of desired, RT=15.7 min.

Hydrate/Methanolate

One aspect of the invention that is of interest relates to a crystalline polymorphic compound of formula A in the form of a free acid hydrate/methanolate solvate.

The hydrate/methanolate solvate of compound A was obtained by direct crystallization of compound A in methanol/water at different solvent compositions.

Alternatively, it can be obtained by adding excess amount of compound A in methanol/water, stirring for several hours, and recovering the solids by filtration. Characterization is in accordance with Table 1 below.

TABLE 1

X-ray powder diffraction: free acid hydrate/ methanolate of Compound A

| 2θ(2 theta)(degrees) | d-spacing (Å) |
|---|---|
| 7.5 | 11.74 |
| 8.8 | 10.10 |
| 11.3 | 7.84 |
| 13.7 | 6.44 |
| 14.9 | 5.95 |
| 15.4 | 5.74 |
| 17.6 | 5.05 |
| 18.4 | 4.83 |
| 20.3 | 4.37 |
| 21.3 | 4.17 |
| 23.4 | 3.81 |
| 25.6 | 3.48 |

Hydrate

An aspect of the invention that is of interest relates to a crystalline polymorphic form of a compound of formula A in the form of a free acid hydrate.

The hydrate of compound A was obtained by removing methanol from the hydrate/methanolate. This can be achieved by drying the hydrate/methanolate at 40° C. at >60% relative humidity. The hydrate can also be converted from the anhydrate of polymorphic form I of compound A by exposing the anhydrate to an atmosphere of >20% relative humidity at room temperature. X Ray characterization is as in Table 2 below.

FIG. 1 is the X-ray powder diffraction (XRPD) pattern for the free acid hydrate polymorphic Form I of Compound A; with selected d-spacings listed in Table 2 below. The compound of formula A exhibits at least three of the d-spacings shown in Table 2, and preferably more than three.

TABLE 2

XRPD: free acid hydrate polymorphic Form I of Compound A

| 2θ(2 theta)(degrees) | d-spacing (Å) |
|---|---|
| 7.5 | 11.74 |
| 8.8 | 10.10 |
| 11.3 | 7.84 |
| 13.7 | 6.44 |
| 14.9 | 5.95 |
| 15.4 | 5.74 |
| 17.6 | 5.05 |
| 18.4 | 4.83 |
| 20.3 | 4.37 |
| 21.3 | 4.17 |
| 23.4 | 3.81 |
| 25.6 | 3.48 |

Figure 2:
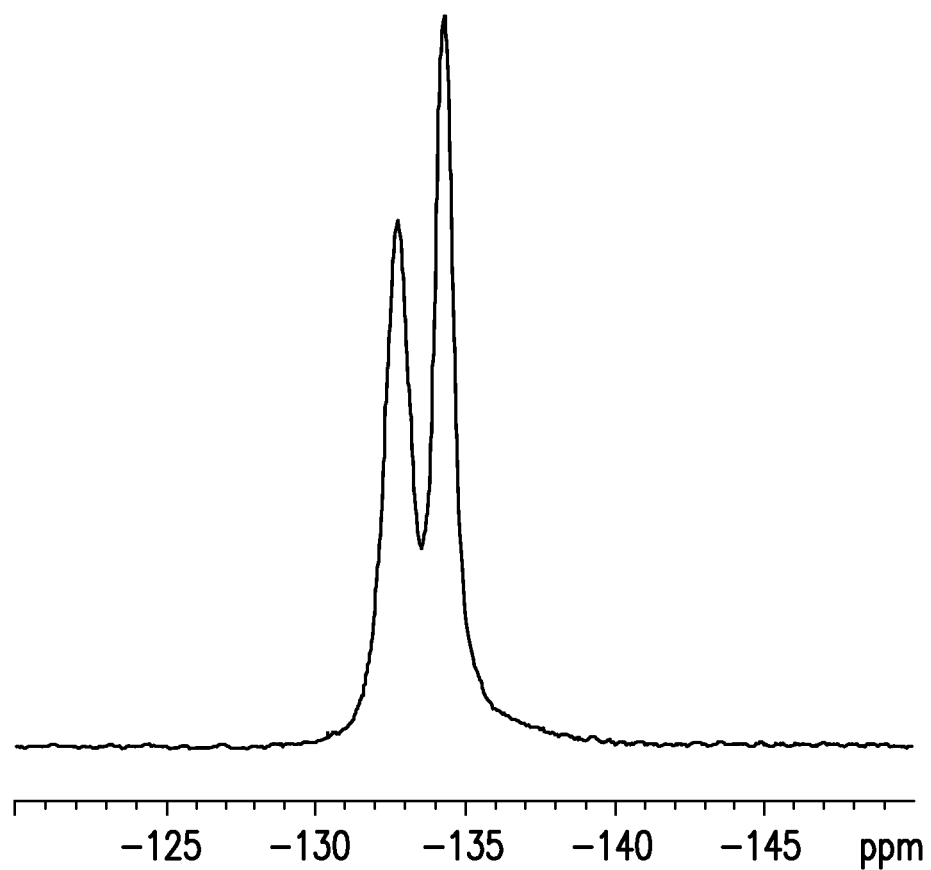
FIG. 2 is the solid-state 19 F CPMAS NMR spectrum of the free acid hydrate polymorphic Form I of Compound A.

FIG. 2 is the solid-state fluorine-19 CPMAS NMR spectrum of the free acid hydrate polymorphic Form I of Compound A. Form I exhibited characteristic signals with chemical shift values of −132.7 and −134.3 ppm.

Figure 3:
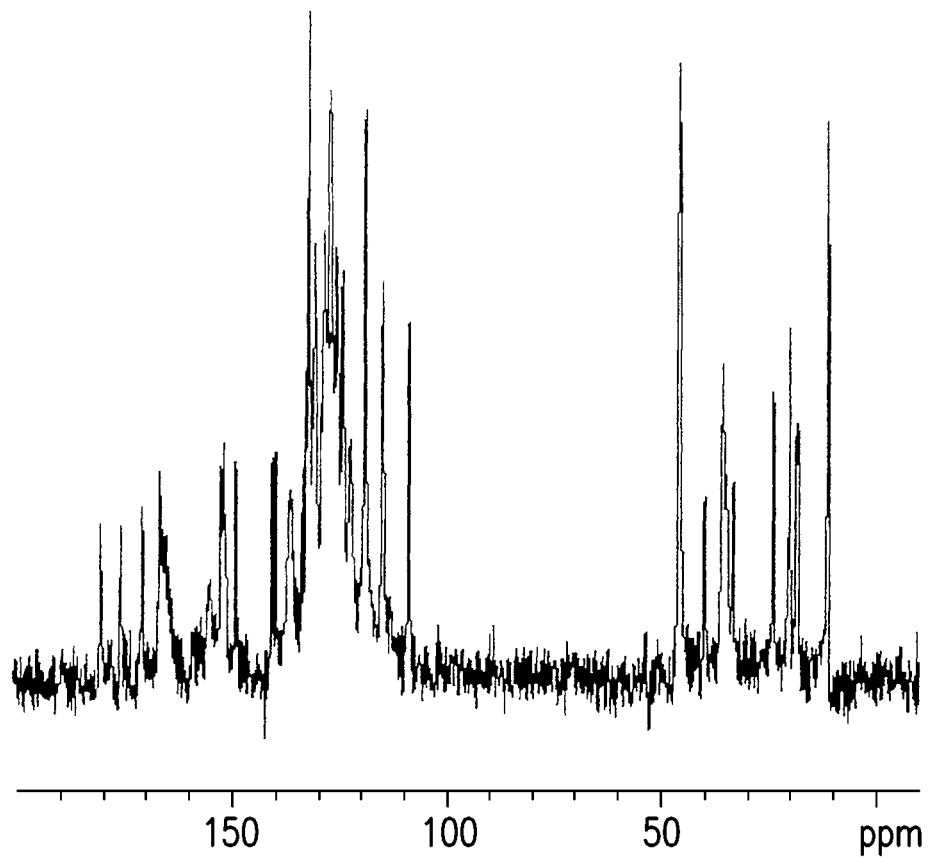
FIG. 3 is the 13C solid state NMR of the free acid hydrate polymorphic Form I of Compound A.
Figure 4:
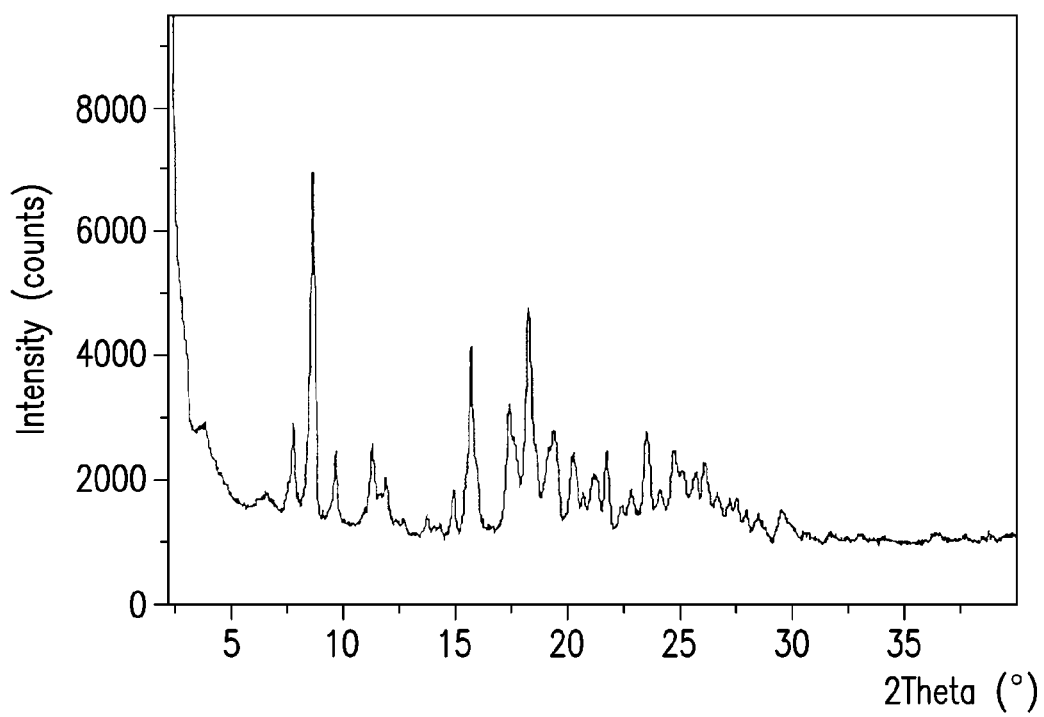
FIG. 4 is the X-ray powder diffraction (XRPD) pattern of anhydrous free acid polymorphic Form I of Compound A.

FIG. 3 is the solid-state carbon-13 CPMAS NMR spectrum of the free acid hydrate polymorphic Form I of Compound A. Form I exhibited characteristic signals with chemical shift values of 11.3, 20.2, 23.9, 33.1, 45.5, 108.6, 118.7, 131.7, 139.3, 148.5, 170.1 and 179.9 ppm.

Another aspect of the invention that is of interest relates to the crystalline free acid hydrate of a compound of formula A wherein at least three of the X-ray powder diffraction pattern d-spacings are as found in Table 2.

Another aspect of the invention that is of interest relates to the crystalline free acid hydrate of a compound of formula A wherein at least five of the X-ray powder diffraction pattern d-spacings are as found in Table 2.

Another aspect of the invention that is of interest relates to the crystalline free acid hydrate of a compound of formula A wherein at least three C13 solid state NMR characteristic signals with chemical shift values are selected from the group consisting of: 11.3, 20.2, 23.9, 33.1, 45.5, 108.6, 118.7, 131.7, 139.3, 148.5, 170.1 and 179.9 ppm.

Anhydrate Form I:

Another aspect of the invention that is of interest relates to a crystalline polymorphic compound of formula A in the form of an anhydrous free acid.

More particularly, an aspect of the invention that is of interest relates to a crystalline polymorphic compound of formula A in the form of an anhydrous free acid, said polymorphic compound having at least three X-ray powder diffraction pattern d spacings in accordance with Table 3.

Even more particularly, an aspect of the invention that is of interest relates to a crystalline polymorphic compound of formula A in the form of an anhydrous free acid, said polymorphic compound having at least five X-ray powder diffraction pattern d spacings in accordance with Table 3.

Figure 5:
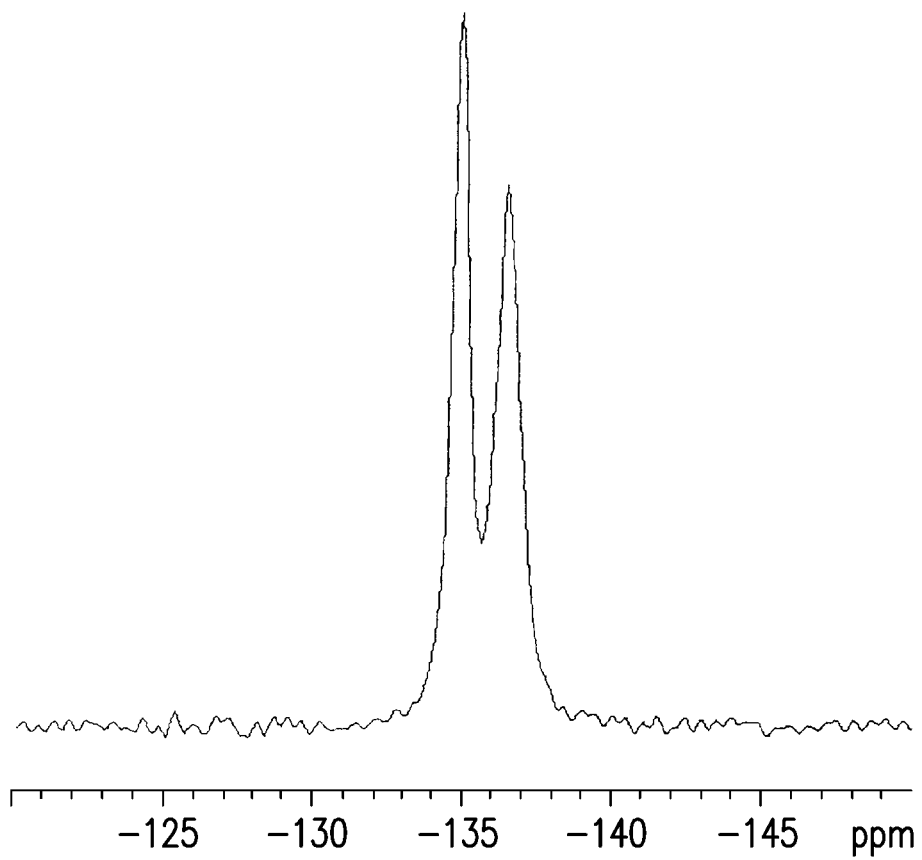
FIG. 5 is the 19F solid state NMR of anhydrous free acid polymorphic Form I of Compound A.
Figure 6:
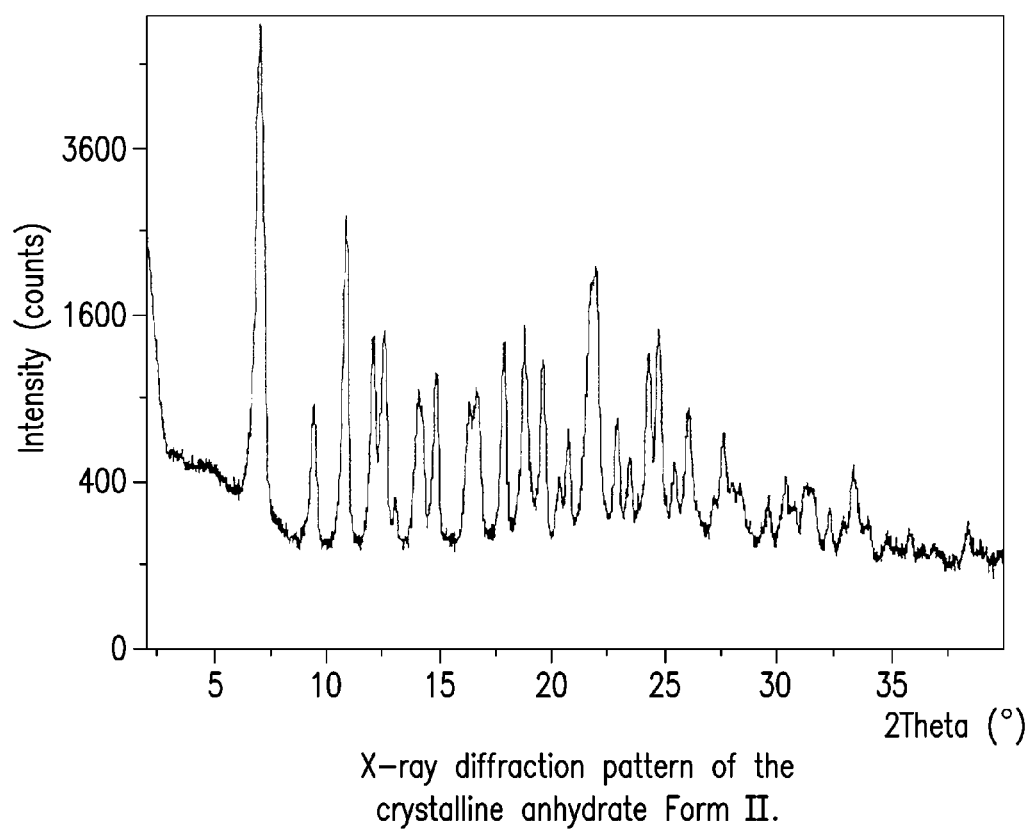
FIG. 6 is the X-ray diffraction pattern of the crystalline anhydrate Form II of Compound A.

Another aspect of the invention relates to a crystalline polymorphic compound of formula A in the form of an anhydrous free acid, said polymorphic compound having a 19F solid state NMR as shown in FIG. 5.

The anhydrate I of compound A was obtained either from hydrate/methanolate of compound A by removing methanol/water or from hydrate of compound A by removing water. This can be achieved by drying the hydrate/methanolate or the hydrate with $N_2$ at room temperature or at higher temperatures. Anhydrate form I of Compound A exhibits at least three of the d-spacings shown in Table 3, and preferably more than three. The solid state 19F NMR characterization for anhydrous free acid polymorphic form I of Compound A exhibited characteristic signals with chemical shift values of −134.8 and −136.3 ppm.

TABLE 3

X-ray powder diffraction: anhydrous free acid polymorphic Form I of Compound A

| 2θ(2 theta)(degrees) | d-spacing (Å) |
|---|---|
| 7.8 | 11.35 |
| 8.7 | 10.19 |
| 9.7 | 9.11 |
| 11.3 | 7.82 |
| 11.9 | 7.41 |
| 14.9 | 5.93 |
| 15.7 | 5.63 |
| 17.4 | 5.10 |
| 20.1 | 4.41 |
| 21.7 | 4.10 |
| 25.6 | 3.47 |

Anhydrate Form II:

Another aspect of the invention that is of interest relates to a crystalline polymorphic compound in accordance with formula A in the form of a free acid anhydrate of form II.

In particular, an aspect of the invention that is of interest relates to a crystalline polymorphic compound in accordance with formula A in the form of a free acid anhydrate of form II, wherein at least three of the x-ray powder diffraction pattern d-spacing peaks are in accordance with table 4.

Even more particularly, an aspect of the invention that is of interest relates to a crystalline polymorphic compound in accordance with formula A in the form of a free acid anhydrate of form II, wherein at least five of the x-ray powder diffraction pattern d-spacing peaks are in accordance with table 4.

Anhydrate Form II is prepared from a solution of the crystalline hydrate form at a concentration of >100 mg/mL in acetonitrile. The solution is sonicated for approximately 5 minutes to induce crystallization. Anhydrate II is metastable. It converts to crystalline Anhydrate III when heated to 160° C. for 1 hour or in solutions of ethanol, isoamyl alcohol and isopropyl acetate. The X Ray Powder Diffraction peaks are shown below in Table 4. Anhydrate form II of compound A exhibits at least 3 of the peaks shown below in table 4, and preferably more than four.

TABLE 4

X-Ray Powder Diffraction peaks for Anhydrate Form II

| d-spacing [Å] | 2θ(2 theta)(degrees) |
|---|---|
| 3.59 | 24.82 |
| 4.05 | 21.95 |
| 4.10 | 21.70 |
| 4.53 | 19.58 |
| 4.72 | 18.79 |
| 5.93 | 14.93 |
| 7.02 | 12.62 |
| 7.31 | 12.11 |
| 8.07 | 10.96 |
| 12.36 | 7.15 |

Figure 7:
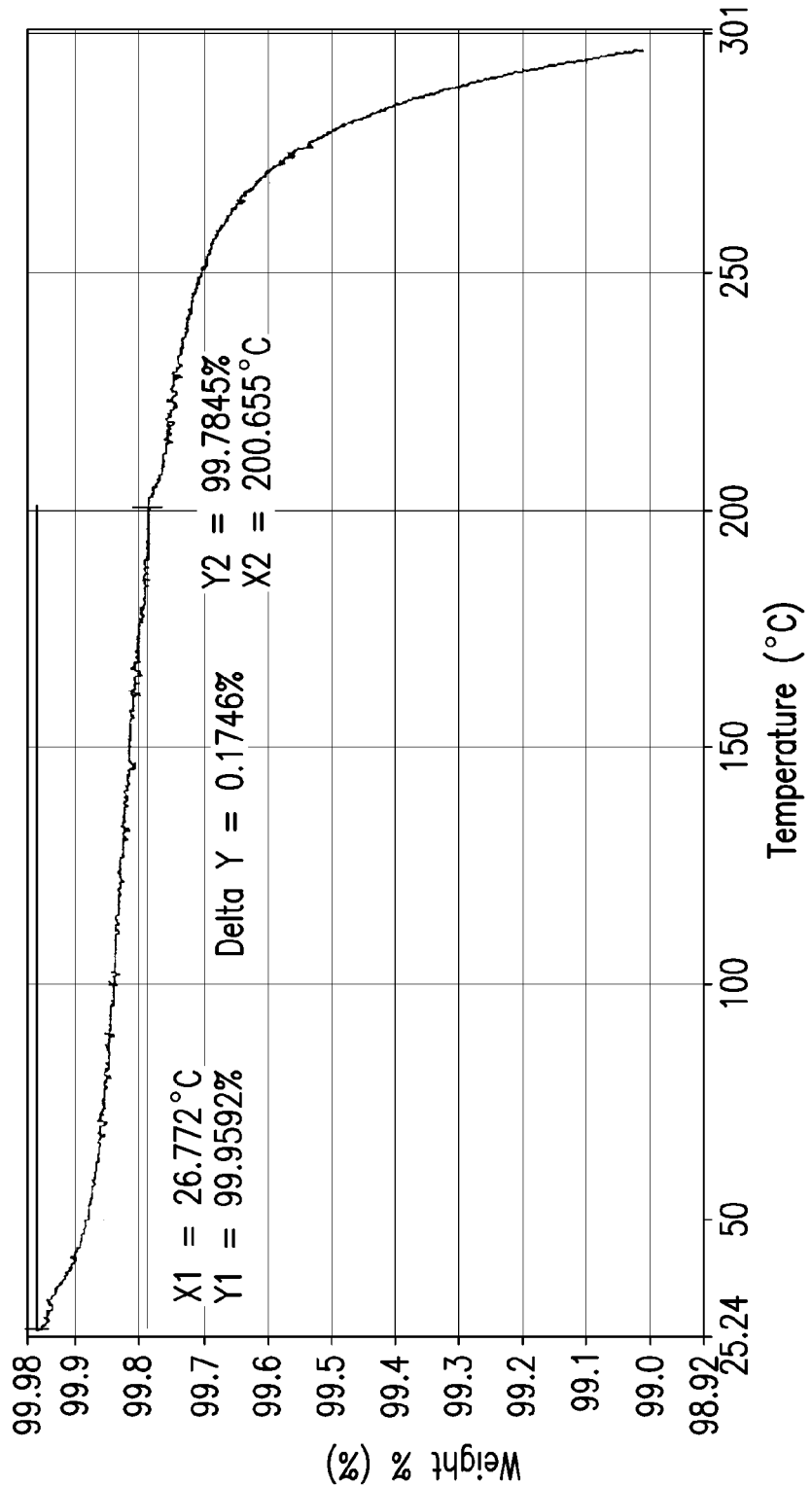
FIG. 7 is the Thermogravimetric analysis curve of the crystalline anhydrate From II of Compound A.

The thermogravimetric analysis curve for crystalline anhydrate form II is shown in FIG. 7.

Figure 8:
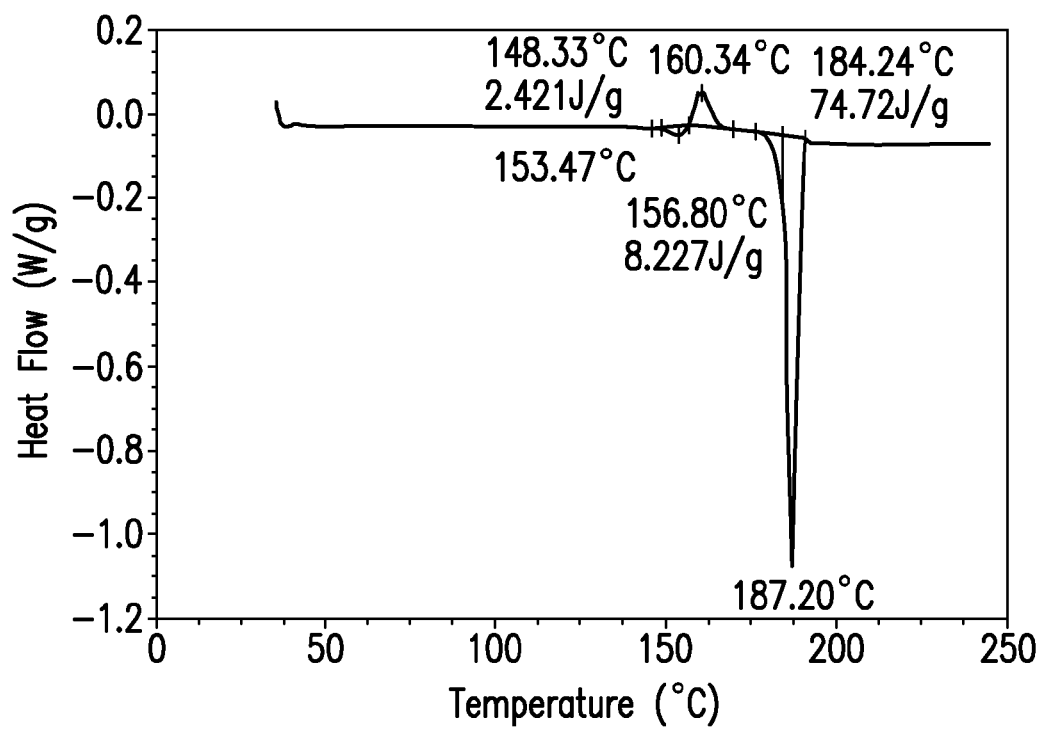
FIG. 8 is the Differential Scanning calorimetry curve of the crystalline anhydrate Form II of Compound A.

The differential scanning calorimetry (DSC) curve of the crystalline anhydrate Form II of Compound I of the present invention is shown in FIG. 8.

Figure 9:
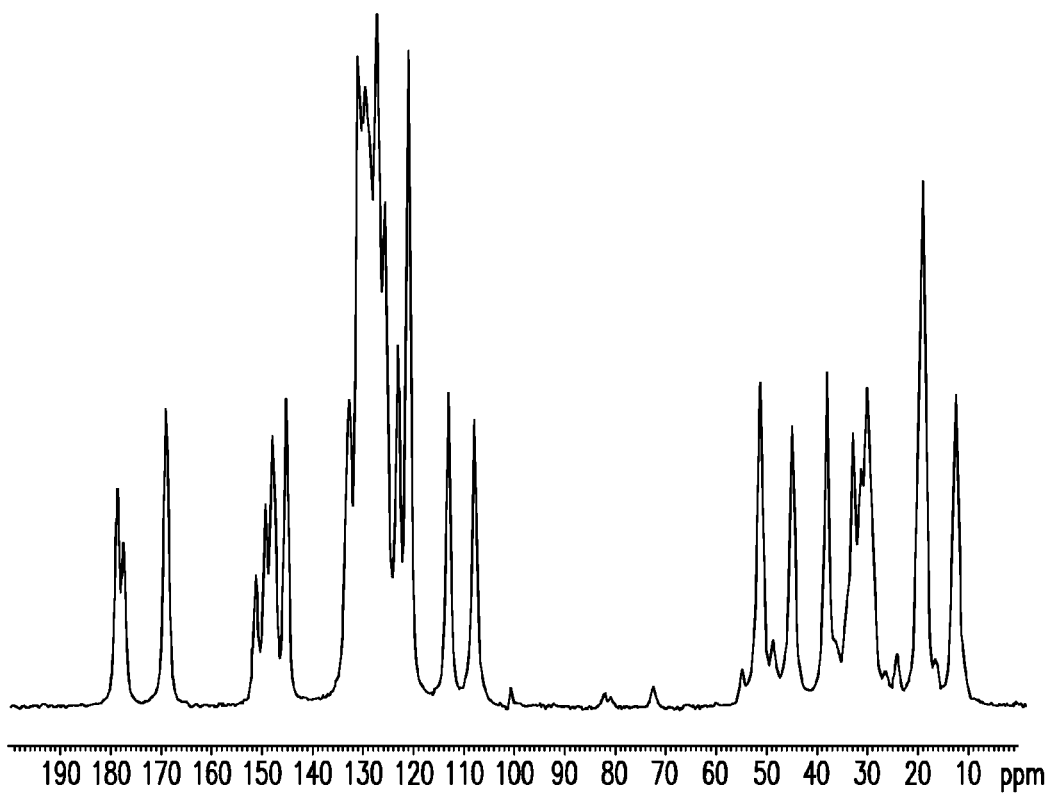
FIG. 9 is the Solid State C-13 CPMAS NMR spectrum for the crystalline anhydrate Form II of Compound A.

Another aspect of the invention that is of interest relates to a crystalline polymorphic compound of formula A of Form II, having at least three C13 solid state NMR peaks selected from the group consisting of: 131.51, 130.07, 127.68, 126.30, 123.81, 121.65, 52.57, 39.62, 31.77, and 20.79 ppm, The 13 CPMAS NMR spectrum for the crystalline anhydrate Form II of Compound A is shown in FIG. 9. Characteristic peaks for anhydrate Form II are observed at 131.51, 130.07, 127.68, 126.30, 123.81, 121.65, 52.57, 39.62, 31.77, and 20.79 ppm.

Figure 10:
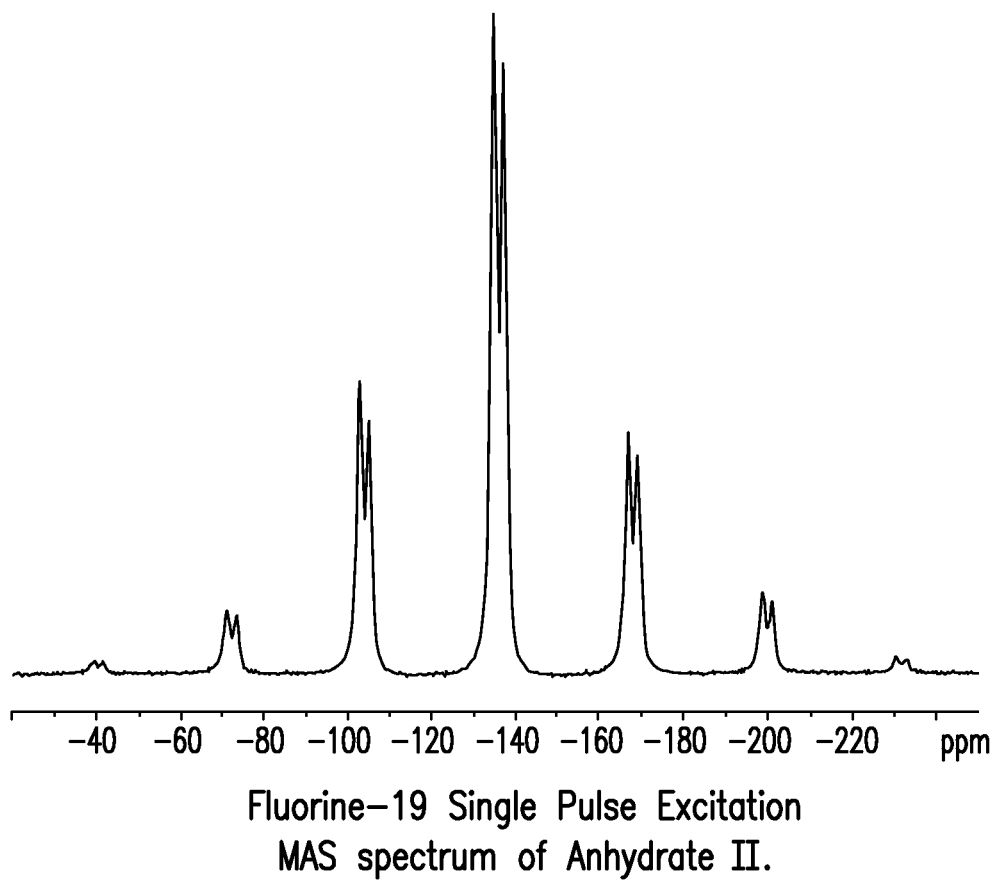
FIG. 10 is the Fluorine-19 Single Pulse Excitation MAS spectrum of Anhydrate II of Compound A.

FIG. 10 shows the fluorine-19 spectra (spinning sideband patterns) for anhydrate Form II of compound I. Center band peaks for anhydrate Form II are observed at −134.80 and −137.08 ppm.

Anhydrate Form III

Another aspect of the invention that is of interest relates to a crystalline polymorphic compound in accordance with formula A in the form of a free acid anhydrate of form III.

In particular, an aspect of the invention that is of interest relates to a crystalline polymorphic compound in accordance with formula A in the form of a free acid anhydrate of form III, wherein at least three of the x-ray powder diffraction pattern d-spacing peaks are in accordance with table 5.

Even more particularly, an aspect of the invention that is of interest relates to a crystalline polymorphic compound in accordance with formula A in the form of a free acid anhydrate of form III, wherein at least five of the x-ray powder diffraction pattern d-spacing peaks are in accordance with table 5.

Anhydrate Form III is prepared by heating anhydrate form II to 160° C. for 1 h. It can also be prepared by slurrying the hydrate or the Anhydrate II in ethanol, isoamyl alcohol and isopropyl acetate.

X-Ray Powder Diffraction for Anhydrate Form III

Figure 11:
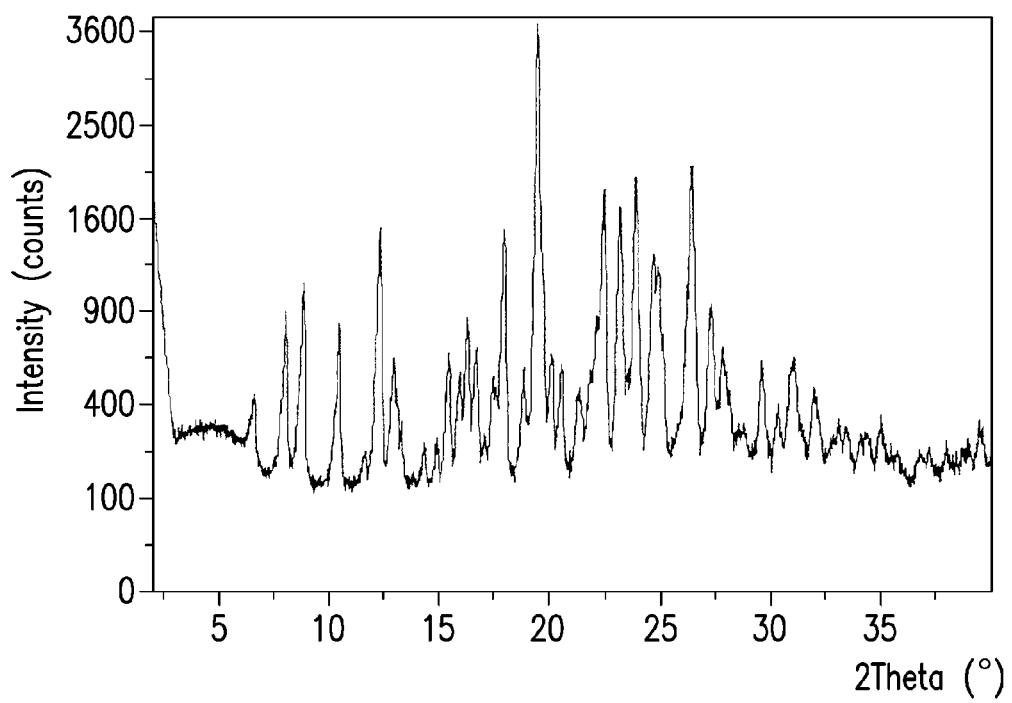
FIG. 11 is the X-ray Powder Diffraction pattern of the crystalline anhydrate Form III of Compound A.

FIG. 11 is a characteristic X-ray diffraction pattern of the crystalline anhydrate Form III of Compound I of the present invention.

The anhydrate Form III exhibited characteristic reflections corresponding to d-spacings are shown below in Table 5. Anhydrate form III of compound A exhibits at least three of the d-spacings shown in table 5, and preferably more than three.

TABLE 5

| 2 theta | d-spacing [Å] |
|---|---|
| 26.42 | 3.37 |
| 24.90 | 3.58 |
| 24.61 | 3.62 |
| 23.87 | 3.73 |
| 23.21 | 3.83 |
| 22.44 | 3.96 |
| 19.66 | 4.52 |
| 19.43 | 4.57 |
| 17.94 | 4.94 |
| 12.2927 | 7.20 |

Thermogravimetric Analysis for Anhydrate Form III

Figure 12:
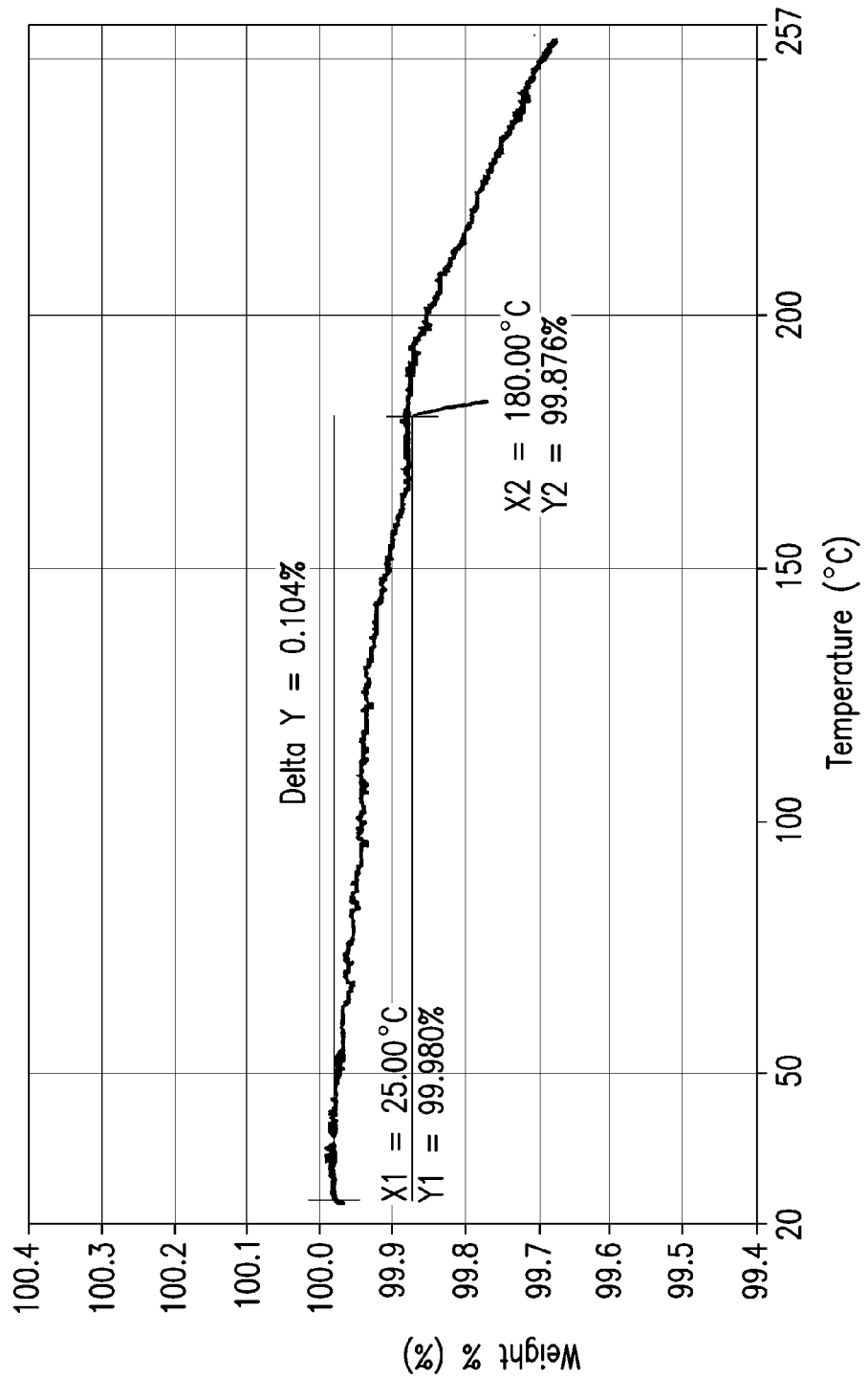
FIG. 12 is the Thermogravimetric analysis curve of the crystalline anhydrate Form III of Compound A.

FIG. 12 is a typical thermogravimetric analysis curve of the crystalline anhydrate Form III of Compound A.

Differential Scanning Calorimetry

Figure 13:
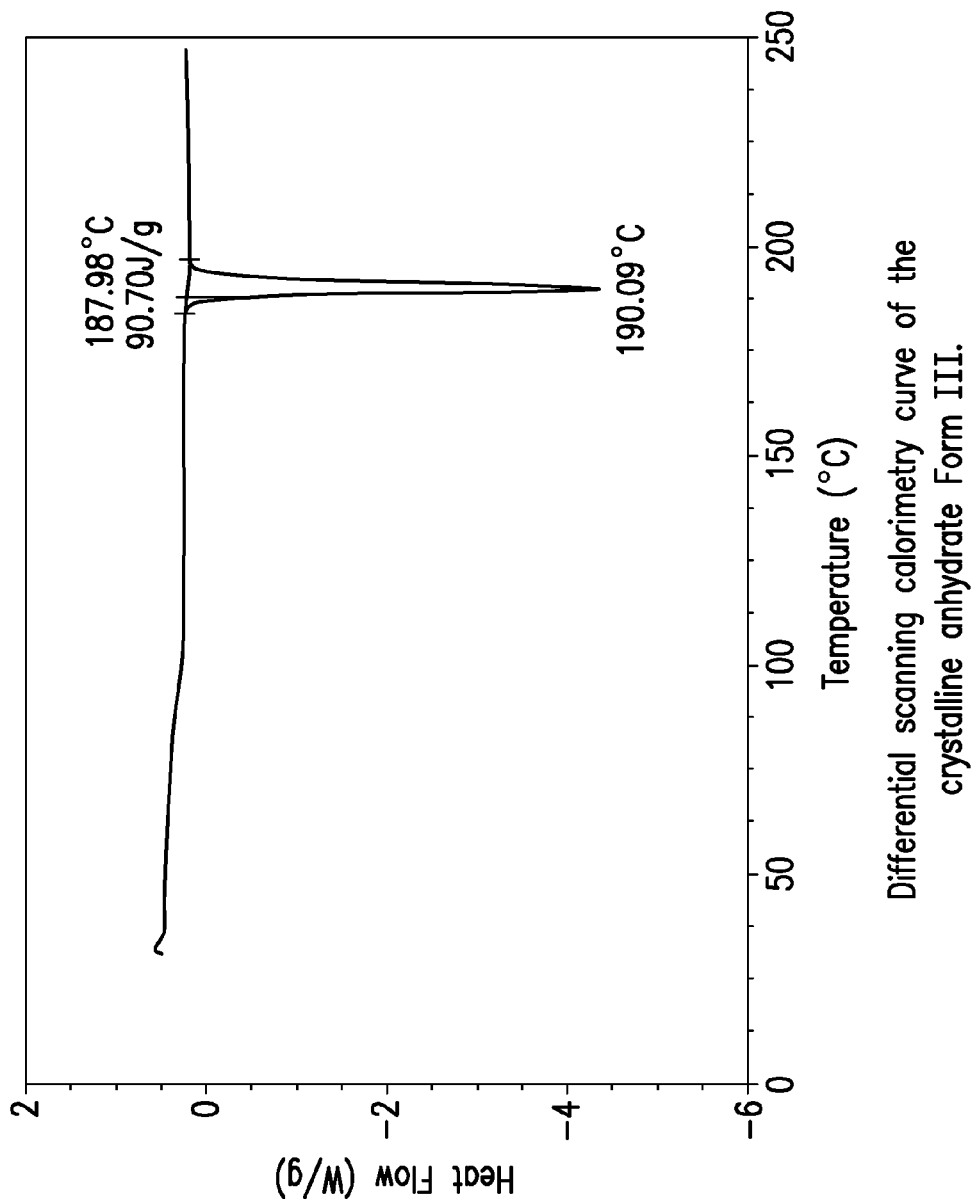
FIG. 13 is the Differential Scanning calorimetry curve of the crystalline anhydrate Form III of Compound A.

FIG. 13 is a typical differential scanning calorimetry (DSC) curve of the crystalline anhydrate Form III of Compound A.

Solid State NMR

Another aspect of the invention that is of interest relates to a crystalline polymorphic compound of formula A of Form III, having at least three C13 solid state NMR peaks selected from the group consisting of: 177.58, 148.52, 146.17, 130.34, 121.11, 113.44, 52.77, 31.30, 21.42, and 14.04 ppm.

Figure 14:
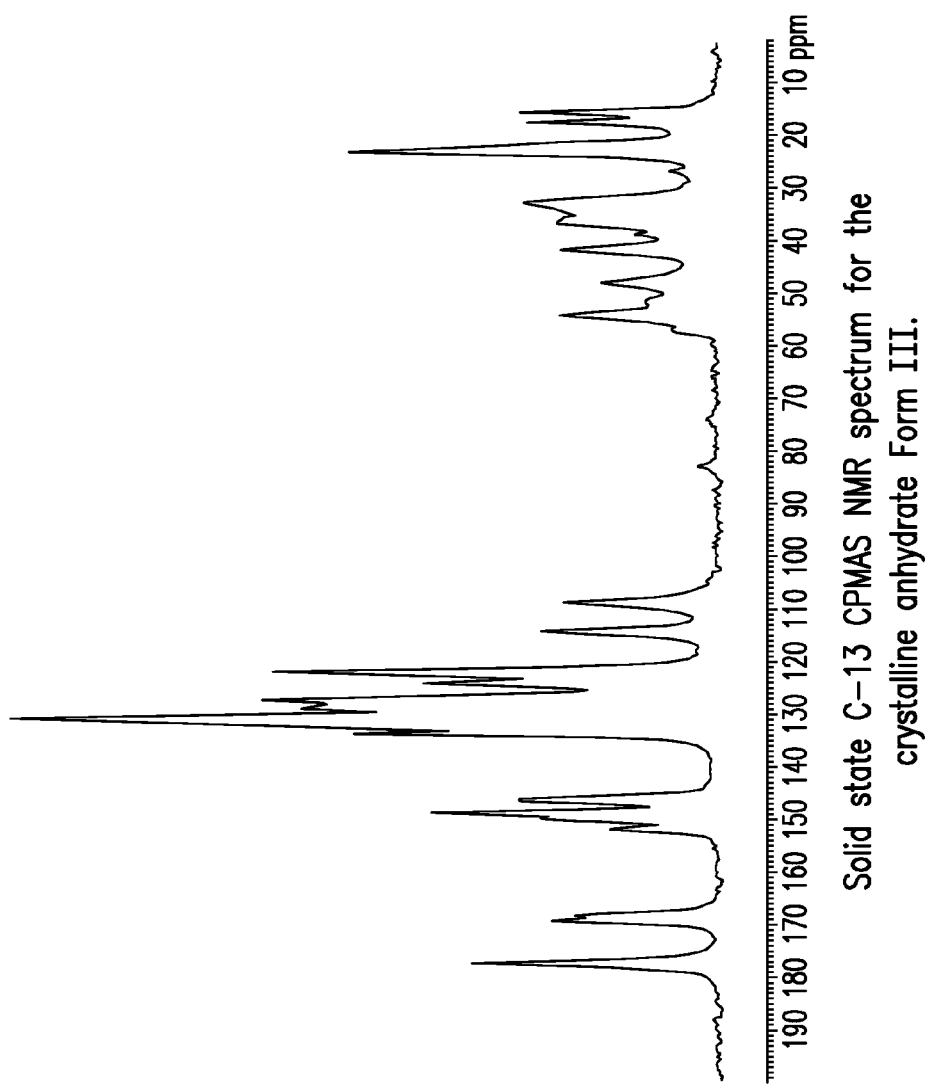
FIG. 14 is the Solid State C-13 CPMAS NMR spectrum for the crystalline anhydrate Form III of Compound A.

FIG. 14 shows the solid state carbon-13 CPMAS NMR spectrum for the crystalline anhydrate Form III of Compound A.

Anhydrate III can be characterized by peaks at 177.58, 148.52, 146.17, 130.34, 121.11, 113.44, 52.77, 31.30, 21.42, and 14.04 ppm.

Figure 15:
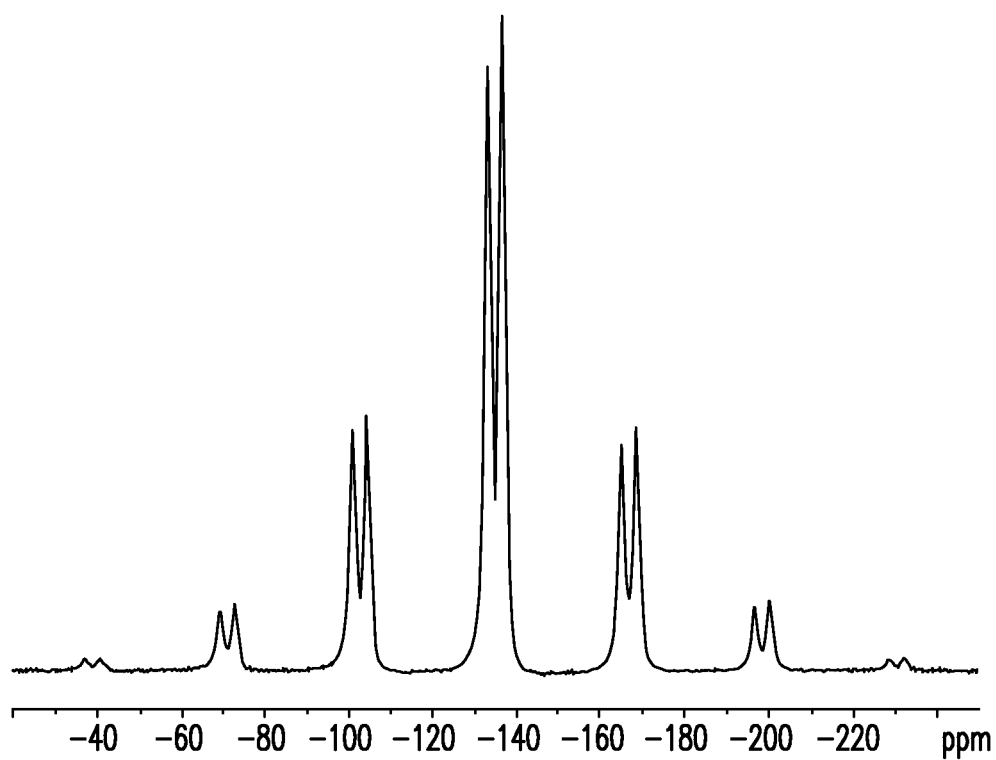
FIG. 15 is the Fluorine-19 Single Pulse Excitation MAS spectrum of crystalline anhydrate Form III of Compound A.

FIG. 15 shows the fluorine-19 spectra (spinning sideband patterns) of crystalline Anhydrate III of Compound A. Anhydrate form III exhibits center band signals at −132.96 and −136.45 ppm.

Another aspect of the invention that is of interest relates to a pharmaceutical composition that is comprised of a polymorphic form of a compound of formula A in combination with a pharmaceutically acceptable carrier.

The following are examples of pharmaceutical dosage forms containing a compound of Formula A:

| Injectable Suspension (im.) | mg/mL | Tablet | Mg/tablet |
|---|---|---|---|
| Compound of Formula A | 10.0 | Compound of Formula A | 25.0 |
| Methylcellulose | 5.0 | Microcrystalline Cellulose | 415 |

| | | | |
|---|---|---|---|
| Tween 80 | 0.5 | Povidone | 14.0 |
| Benzyl alcohol | 9.0 | Pregelatinized Starch | 4.35 |
| Benzalkonium chloride | 1.0 | Magnesium Stearate | 2.5 |
| Water for injection | t.d. 1.0 mL | Total | 500 mg |

| Capsule | mg/ capsule | Aerosol | Per Canister |
|---|---|---|---|
| Compound of Formula A | 25.0 | Compound of Formula A | 250 mg |
| Lactose | 735 | Lecithin, NF Liq. Conc. | 1.2 mg |
| Mg Stearate | 1.5 | Trichloromethane, NF | 4.025 g |
| Total | 600 mg | Dichlorodifluoromethane, NF | 12.15 g |

Certain embodiments of the invention has been described in detail; however, numerous other embodiments are contemplated as falling within the invention. Thus, the claims are not limited to the specific embodiments described herein. All patents, patent applications and publications that are cited herein are hereby incorporated by reference in their entirety.

What is claimed is:

1. A process for synthesizing a compound of formula A:

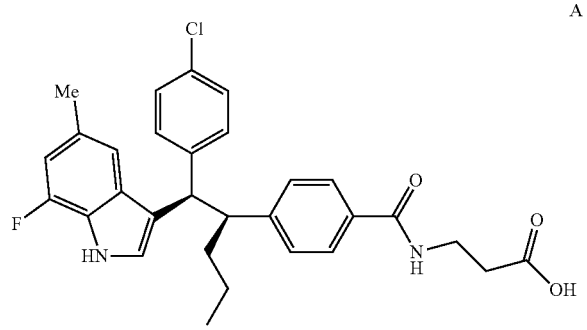 [SMILES: CCC[C@H](c1ccc(C(=O)NCCC(=O)O)cc1)[C@H](c1ccc(Cl)cc1)c1c[nH]c2c(F)cc(C)cc12]

comprising deprotecting a compound of formula 11a:

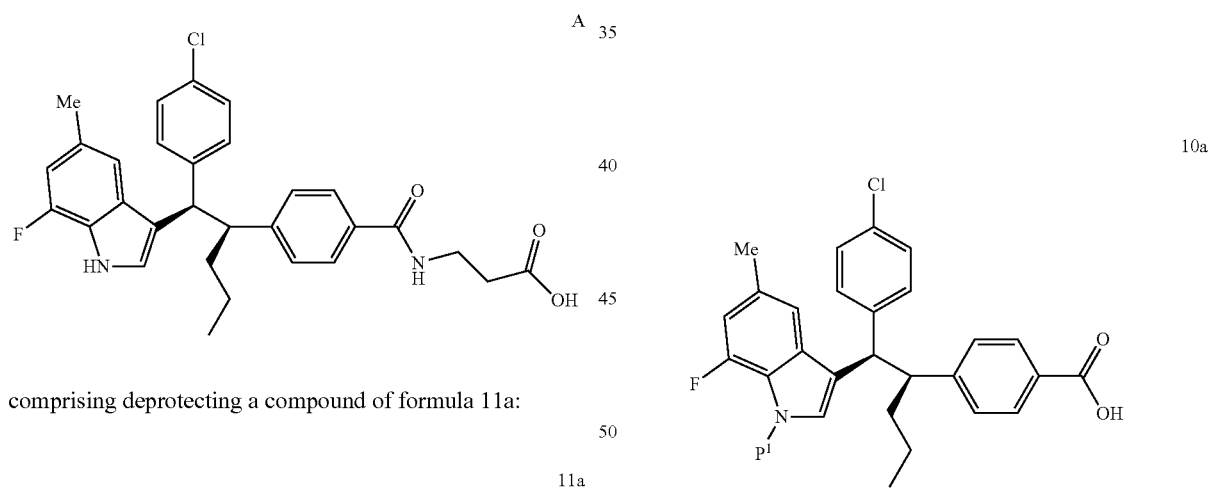

wherein P¹ and P² represent protecting groups, to produce a compound of formula A.

2. A process for synthesizing a compound of formula A:

A comprising reacting a compound of formula 10a:

10a wherein P¹ represents a protecting group with a beta alanine ester of the formula

wherein P² represents a protecting group, with a peptide coupling agent, to produce a compound of formula 11a:

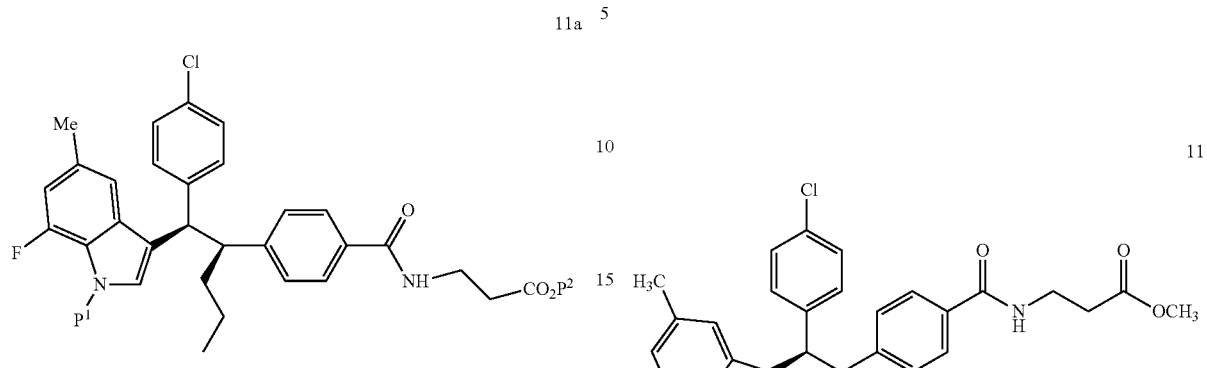

and deprotecting compound 11a to produce a compound of formula A.

3. A process for the synthesis of a compound of formula A:

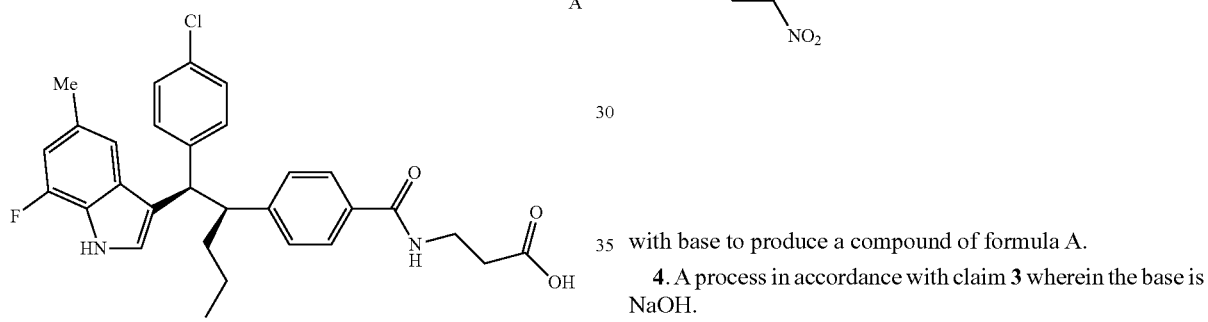

comprising reacting a compound of the formula 11:

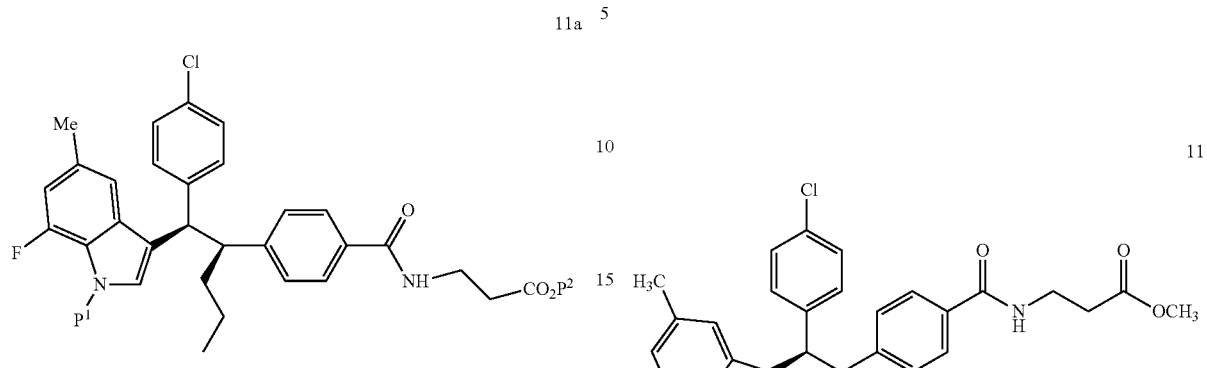

with base to produce a compound of formula A.

4. A process in accordance with claim 3 wherein the base is NaOH.

* * * * *